United States Patent
Merla et al.

(10) Patent No.: US 8,124,788 B2
(45) Date of Patent: Feb. 28, 2012

(54) SPIROCYCLIC CYCLOHEXANE COMPOUNDS WITH ANALGESIC ACTIVITY

(75) Inventors: Beatrix Merla, Aachen (DE); Stefan Oberboersch, Aachen (DE); Bernd Sundermann, Aachen (DE); Werner Englberger, Stolberg (DE); Hagen-Heinrich Hennies, Simmerath (DE); Babette-Yvonne Koegel, Langerwehe-Hamich (DE); Stephan Schunk, Aachen (DE); Heinz Graubaum, Berlin (DE)

(73) Assignee: Gruenenthal GmbH, Aachen (DE)

( * ) Notice: Subject to any disclaimer, the term of this patent is extended or adjusted under 35 U.S.C. 154(b) by 613 days.

(21) Appl. No.: 12/258,936

(22) Filed: Oct. 27, 2008

(65) Prior Publication Data
US 2009/0111842 A1 Apr. 30, 2009

Related U.S. Application Data

(63) Continuation of application No. PCT/EP2007/003630, filed on Apr. 25, 2007.

(30) Foreign Application Priority Data

Apr. 27, 2006 (DE) .................. 10 2006 019 597

(51) Int. Cl.
C07D 209/56 (2006.01)
A61K 31/404 (2006.01)
(52) U.S. Cl. ................... 548/407; 514/409
(58) Field of Classification Search .......... 548/407; 514/409
See application file for complete search history.

(56) References Cited

U.S. PATENT DOCUMENTS

| 7,288,560 B2 | 10/2007 | Hinze et al. |
| 7,332,519 B2 | 2/2008 | Hinze et al. |
| 2006/0004034 A1 | 1/2006 | Hinze et al. |

FOREIGN PATENT DOCUMENTS

| WO | WO 2004/043967 A1 | 5/2004 |
| WO | WO 2005/063769 A1 | 7/2005 |
| WO | WO 2005/066183 A1 | 7/2005 |
| WO | WO 2006/018184 A2 | 2/2006 |
| WO | WO 2006108565 A1 * | 10/2006 |

OTHER PUBLICATIONS

International Search Report dated Aug. 20, 2007 (Three (3) pages).

\* cited by examiner

*Primary Examiner* — Robert Havlin
(74) *Attorney, Agent, or Firm* — Crowell & Moring LLP

(57) ABSTRACT

Spirocyclic cyclohexane compounds corresponding to formula I

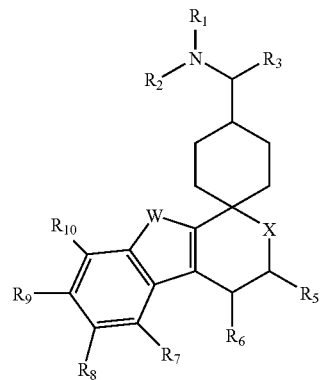

a process for manufacturing such compounds, pharmaceutical compositions that contain such compounds, and the use of such spirocyclic cyclohexane compounds for the production of pharmaceuticals, and particularly for the treatment of pain.

22 Claims, No Drawings

US 8,124,788 B2

SPIROCYCLIC CYCLOHEXANE COMPOUNDS WITH ANALGESIC ACTIVITY

CROSS REFERENCE TO RELATED APPLICATIONS

This application is a continuation of international patent application no. PCT/EP2007/003630, filed Apr. 25, 2007, designating the United States of America, and published in German on Nov. 8, 2007 as WO 2007/124903, the entire disclosure of which is incorporated herein by reference. Priority is claimed based on Federal Republic of Germany patent application no. DE 10 2006 019 597.3, filed Apr. 27, 2006.

BACKGROUND OF THE INVENTION

The present invention relates to spirocyclic cyclohexane derivatives, processes for the preparation thereof, pharmaceutical compositions containing these compounds and the use of substituted spirocyclic cyclohexane derivatives for the preparation of pharmaceutical compositions.

Treatment of chronic and non-chronic states of pain is of great importance in medicine. There is a worldwide need for pain therapies which are highly effective. The urgent need for action for targeted treatment of chronic and non-chronic states of pain appropriate for the patient, by which is to be understood successful and satisfactory pain treatment for the patient, is documented in the large number of scientific works which have been published recently in the field of applied analgesics and of basic research into nociception.

Conventional opioids, such as morphine, have a good action in the therapy of severe to very severe pain. However, their use is limited by the known side effects, e.g. respiratory depression, vomiting, sedation, constipation and development of tolerance. Furthermore, they are less active on neuropathic or incidental pain, from which tumour patients in particular suffer.

WO 04 043967 likewise discloses spirocyclic cyclohexane derivatives, but which carry an amino function instead of an aminomethyl group in the 1-position of the cyclohexane ring.

SUMMARY OF THE INVENTION

One object on which the invention is based was to provide novel substances having analgesic activity which are suitable for pain therapy—in particular also chronic and neuropathic pain.

The invention therefore provides spirocyclic cyclohexane compounds corresponding to formula I

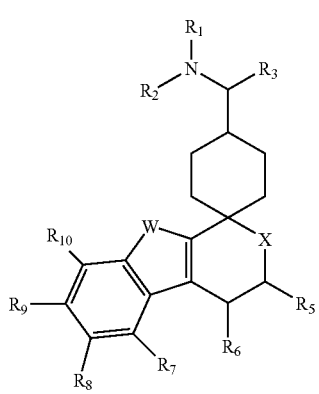

I wherein
$R^1$ and $R^2$ each independently denote H; $C_{1-6}$-alkyl, in each case saturated or unsaturated, branched or unbranched, wherein $R^1$ and $R^2$ do not simultaneously denote H, or
$R^1$ and $R^2$ together denote $CH_2CH_2OCH_2CH_2$, $CH_2CH_2NR^{11}CH_2CH_2$ or $(CH_2)_{3-6}$, wherein
$R^{11}$ denotes H; $C_{1-5}$-alkyl or $C_{3-8}$-cycloalkyl, in each case saturated or unsaturated, branched or unbranched, mono- or polysubstituted or unsubstituted; aryl or heteroaryl, in each case mono- or polysubstituted or unsubstituted; or aryl or $C_{3-8}$-cycloalkyl or heteroaryl, bonded via a $C_{1-3}$-alkyl group and in each case unsubstituted or mono- or polysubstituted;
$R^3$ represents aryl or heteroaryl, in each case unsubstituted or mono- or polysubstituted; aryl or heteroaryl linked via a $C_{1-3}$-alkyl group and in each case unsubstituted or mono- or polysubstituted; $C_{3-8}$-cycloalkyl or $C_{1-8}$-alkyl, unsubstituted or mono- or polysubstituted;
W represents $NR^4$, O or S; and
$R^4$ represents H; $C_{1-5}$-alkyl, saturated or unsaturated, branched or unbranched, unsubstituted or mono- or polysubstituted; aryl or heteroaryl, in each case substituted or unsubstituted; aryl, heteroaryl or cycloalkyl, bonded via a $C_{1-3}$-alkyl group and in each case mono- or polysubstituted or unsubstituted; $COR^{12}$, $CSR^{12}$ or $SO_2R^{12}$, wherein
$R^{12}$ denotes H; $C_{1-8}$-alkyl, in each case saturated or unsaturated, branched or unbranched, mono- or polysubstituted or unsubstituted; $C_{3-8}$-cycloalkyl, in each case saturated or unsaturated, mono- or polysubstituted or unsubstituted; aryl or heteroaryl, in each case mono- or polysubstituted or unsubstituted; or aryl, $C_{3-8}$-cycloalkyl or heteroaryl, bonded via $C_{1-3}$-alkyl and in each case mono- or polysubstituted or unsubstituted; $(CHR^a)_qOR^{13}$ wherein q=0, 1 or 2, and $R^a$=H, methyl or ethyl; $NR^{14}R^{15}$;
$R^5$ represents H; $C_{1-5}$-alkyl, saturated or unsaturated, branched or unbranched, unsubstituted or mono- or polysubstituted; $COOR^{13}$, $CONR^{13}$, $OR^{13}$; $C_{3-8}$-cycloalkyl, saturated or unsaturated, unsubstituted or mono- or polysubstituted; aryl or heteroaryl, unsubstituted or mono- or polysubstituted; or aryl, $C_{3-8}$-cycloalkyl or heteroaryl, bonded via $C_{1-3}$-alkyl and unsubstituted or mono- or polysubstituted;
$R^6$ represents H; $OR^{13}$, $COOR^{13}$, $NR^{14}R^{15}$; $C_{1-5}$-alkyl, saturated or unsaturated, branched or unbranched, unsubstituted or mono- or polysubstituted; $C_{3-8}$-cycloalkyl, saturated or unsaturated, unsubstituted or mono- or polysubstituted; phenyl; or aryl or heteroaryl, bonded via $C_{1-3}$-alkyl;
$R^7$, $R^8$, $R^9$ and $R^{10}$ each independently denote H, F, Cl, Br, $NO_2$, $CF_3$, $OR^{13}$, CN, $COOR^{13}$, $NR^{14}R^{15}$; $C_{1-5}$-alkyl, phenyl or benzyl; wherein
$R^{13}$ denotes H; $C_{1-5}$-alkyl, in each case saturated or unsaturated, branched or unbranched, unsubstituted or mono- or polysubstituted; $C_{3-8}$-cycloalkyl, in each case saturated or unsaturated, unsubstituted or mono- or polysubstituted; aryl or heteroaryl, unsubstituted or mono- or polysubstituted; or aryl, $C_{3-8}$-cycloalkyl or heteroaryl, bonded via $C_{1-3}$-alkyl and in each case unsubstituted or mono- or polysubstituted;
$R^{14}$ and $R^{15}$ each independently denote H or $C_{1-5}$-alkyl, or
$R^{14}$ and $R^{15}$ together form $CH_2CH_2OCH_2CH_2$, $CH_2CH_2NR^{16}CH_2CH_2$ or $(CH_2)_{3-6}$, wherein $R^{16}$ denotes H; $C_{1-5}$-alkyl, saturated or unsaturated;
X represents O, S, SO, $SO_2$ or $NR^{17}$; wherein
$R^{17}$ represents H; $C_{1-5}$-alkyl, saturated or unsaturated, branched or unbranched, in each case mono- or polysubstituted or unsubstituted; $COR^{12}$ or $SO_2R^{12}$,
in the form of the racemate; of the enantiomers, diastereomers, mixtures of the enantiomers or diastereomers or of an individual enantiomer or diastereomer; of the bases and/or salts of physiologically acceptable acids.

If a substituent, such as e.g. $R^{13}$, appears several times in various positions within a compound, such as e.g. groups $R^7$-$R^{10}$ in the meaning $OR^{13}$, the substituent, here $R^{13}$ can assume different meanings for two or more groups within a substance.

The compounds have an affinity for the µ opioid receptor.

In the context of this invention, the expressions "$C_{1-3}$-alkyl" "$C_{1-5}$-alkyl" or "$C_{1-8}$-alkyl" include acyclic saturated or unsaturated hydrocarbon moieties, which can be branched- or straight-chain and unsubstituted or mono- or polysubstituted, having 1 to 3 C atoms or 1 to 5 C atoms or 1 to 8 C atoms, i.e. $C_{1-3}$-alkanyls, $C_{2-3}$-alkenyls and $C_{2-3}$-alkynyls, or $C_{1-5}$-alkanyls, $C_{2-5}$-alkenyls and $C_{2-5}$-alkynyls, or $C_{1-8}$-alkanyls, $C_{2-8}$-alkenyls and $C_{2-8}$-alkynyls. In this context, alkenyls have at least one C—C double bond and alkynyls have at least one C—C triple bond. Alkyl is advantageously chosen from the group which includes methyl, ethyl, n-propyl, 2-propyl, n-butyl, iso-butyl, sec-butyl, tert-butyl, n-pentyl, iso-pentyl, neo-pentyl, ethylenyl (vinyl), ethynyl, propenyl (—CH$_2$CH=CH$_2$, —CH=CH—CH$_3$, —C(=CH$_2$)—CH$_3$), propynyl (—CH—C≡CH, —C≡C—CH$_3$), butenyl, butynyl, pentenyl, pentynyl, hexyl, hexenyl, hexynyl, heptyl, octyl and 1-ethyl-pentyl. Methyl, ethyl and propyl are particularly advantageous.

In the context of this invention, the expression "aryl" denotes aromatic hydrocarbons, inter alia phenyls and naphthyls. The aryl groups can also be condensed with further saturated, (partially) unsaturated or aromatic ring systems. Each aryl group can be unsubstituted or mono- or polysubstituted, wherein the substituents on the aryl can be identical or different and can be in any desired and possible position of the aryl. Aryl is advantageously chosen from the group which contains phenyl, 1-naphthyl, 2-naphthyl, which can in each case be unsubstituted or mono- or polysubstituted. The phenyl group is particularly advantageous.

The expression "heteroaryl" represents a 5-, 6- or 7-membered cyclic aromatic group which contains at least 1, an optionally 2, 3, 4 or 5 hetero atoms, wherein the hetero atoms are identical or different and the heterocyclic ring can be unsubstituted or mono- or polysubstituted. If heterocyclic ring is substituted, the substituents can be identical or different and can be in any desired and possible position on the heteroaryl ring. The heterocyclic ring can also be part of a bi- or polycyclic system. Preferred hetero atoms are nitrogen, oxygen and sulfur. The heteroaryl group is preferably selected from the group consisting of pyrrolyl, indolyl, furyl (furanyl), benzofuranyl, thienyl (thiophenyl), benzothienyl, benzothiadiazolyl, benzothiazolyl, benzotriazolyl, benzodioxolanyl, benzodioxanyl, phthalazinyl, pyrazolyl, imidazolyl, thiazolyl, oxadiazolyl, isoxazolyl, pyridyl, pyridazinyl, pyrimidinyl, pyrazinyl, pyranyl, indazolyl, purinyl, indolizinyl, quinolinyl, isoquinolinyl, quinazolinyl, carbazolyl, phenazinyl, phenothiazinyl or oxadiazolyl, wherein bonding to the compounds of the general structure I can take place via any desired and possible ring member of the heteroaryl group. The thienyl group is particularly preferred.

For the purpose of the present invention, the expression "aryl or heteroaryl bonded via $C_{1-3}$-alkyl" means that $C_{1-3}$-alkyl and aryl or heteroaryl have the meanings defined above and the aryl or heteroaryl radical is bonded to the compound of the general structure I via a $C_{1-3}$-alkyl group. Benzyl and phenethyl are particularly advantageous in the context of this invention.

In connection with "alkyl", in the context of this invention the term "substituted" is understood as meaning replacement of a hydrogen atom by F, Cl, Br, I, —CN, NH$_2$, NH—$C_{1-6}$-alkyl, NH—$C_{1-6}$-alkyl-OH, $C_{1-6}$-alkyl, N($C_{1-6}$-alkyl)$_2$, N($C_{1-6}$-alkyl-OH)$_2$, NO$_2$, SH, S—$C_{1-6}$-alkyl, S-benzyl, O—$C_{1-6}$-alkyl, OH, O—$C_{1-6}$-alkyl-OH, =O, O-benzyl, C(=O)$C_{1-6}$-alkyl, CO$_2$H, CO$_2$—$C_{1-6}$-alkyl or benzyl, where polysubstituted alkyl groups are to be understood as meaning those alkyl groups which are substituted several times, e.g. two or three times, either on different or on the same atoms, for example three times on the same C atom, as in the case of CF$_3$ or —CH$_2$CF$_3$, or at different places, as in the case of —CH(OH)—CH=CH—CHCl$_2$. Polysubstitution can be by the same or by different substituents.

With respect to "aryl" and "heteroaryl", in the context of this invention "mono- or polysubstituted" means the replacement once or several times, e.g. two, three or four times, of one or more hydrogen atoms of the ring system by F, Cl, Br, I, CN, NH$_2$, NH—$C_{1-6}$-alkyl, NH—$C_{1-6}$-alkyl-OH, N($C_{1-6}$-alkyl)$_2$, N($C_{1-6}$-alkyl-OH)$_2$, NO$_2$, SH, S—$C_{1-6}$-alkyl, OH, O—$C_{1-6}$-alkyl, O—$C_{1-6}$-alkyl-OH, C(=O)$C_{1-6}$-alkyl, CO$_2$H, CO$_2$—$C_{1-6}$-alkyl, CF$_3$, $C_{1-6}$-alkyl; on one or optionally various atoms (wherein a substituent can optionally be substituted in its turn). In this context, polysubstitution may be by the same or by different substituents. In this context, preferred substituents for "aryl" and "heteroaryl" are —F and —Cl.

In the context of this invention, the term salt formed with a physiologically acceptable acid is understood as meaning salts of the particular active compound with inorganic or organic acids, which are physiologically acceptable—in particular when used on humans and/or mammals. The hydrochloride is particularly preferred. Examples of physiologically acceptable acids include: hydrochloric acid, hydrobromic acid, sulfuric acid, methanesulfonic acid, formic acid, acetic acid, oxalic acid, succinic acid, tartaric acid, mandelic acid, fumaric acid, lactic acid, citric acid, glutamic acid, 1,1-dioxo-1,2-dihydro1$\lambda^6$-benzo[d]isothiazol-3-one (saccharic acid), monomethylsebacic acid, 5-oxo-proline, hexane-1-sulfonic acid, nicotinic acid, 2-, 3- or 4-aminobenzoic acid, 2,4,6-trimethylbenzoic acid, α-liponic acid, acetylglycine, hippuric acid, phosphoric acid and/or aspartic acid. Citric acid and hydrochloric acid are particularly preferred.

The term (CH$_2$)$_{3-6}$ or (CH$_2$)$_{4-5}$ is to be understood as meaning —CH$_2$—CH$_2$—CH$_2$—, —CH$_2$—CH$_2$—CH$_2$—CH$_2$—, —CH$_2$—CH$_2$—CH$_2$—CH$_2$—CH$_2$— and —CH$_2$—CH$_2$—CH$_2$—CH$_2$—CH$_2$—CH$_2$—, or, respectively, —CH$_2$—CH$_2$—CH$_2$—CH$_2$—, —CH$_2$—CH$_2$—CH$_2$—CH$_2$—CH$_2$.

Preferred substituted cyclohexane derivatives are those corresponding to formula I in which $R^1$ and $R^2$ each independently denote H or $C_{1-5}$-alkyl, wherein $R^1$ and $R^2$ do not simultaneously denote H, or $R^1$ and $R^2$ together denote CH$_2$CH$_2$OCH$_2$CH$_2$, or (CH$_2$)$_{3-5}$, in particular (CH$_2$)$_3$. Particularly preferred substituted cyclohexane derivatives are those in which $R^1$ and $R^2$ denote CH$_3$.

Preferred cyclohexane compounds also are those wherein $R^3$ denotes phenyl, thienyl or pyridyl, in each case unsubstituted or mono- or polysubstituted by F, Cl, CN, NH—$C_{1-6}$-alkyl, NH—$C_{1-6}$-alkyl-OH, N($C_{1-6}$-alkyl)$_2$, N($C_{1-6}$-alkyl-OH)$_2$, NO$_2$, SH, S—$C_{1-6}$-alkyl, OH, O—$C_{1-6}$-alkyl, O—$C_{1-6}$-alkyl-OH, C(=O)$C_{1-6}$-alkyl, CO$_2$H, CO$_2$—$C_{1-6}$-alkyl, CF$_3$, $C_{1-6}$-alkyl; an aryl radical bonded via a $C_{1-3}$-alkyl chain and in each case unsubstituted or mono- or polysubstituted by F, Cl, CN, NH—$C_{1-6}$-alkyl, NH—$C_{1-6}$-alkyl-OH, N($C_{1-6}$-alkyl)$_2$, N($C_{1-6}$-alkyl-OH)$_2$, NO$_2$, SH, S—$C_{1-6}$-alkyl, OH, O—$C_{1-6}$-alkyl, O—$C_{1-6}$-alkyl-OH, C(=O)$C_{1-6}$-alkyl, CO$_2$H, CO$_2$—$C_{1-6}$-alkyl, CF$_3$, $C_{1-6}$-alkyl; cyclopentyl or cyclohexyl; or ethyl, propyl, butyl, pentyl or hexyl, in each case unsubstituted or mono- or polysubstituted by OH, OCH$_3$ or OC$_2$H$_5$. Preferably R$^3$ denotes phenyl or thienyl, in each case unsubstituted or mono- or polysubstituted by F, Cl, CN, NO$_2$, SH, S—C$_{1-6}$-alkyl, OH, O—C$_{1-6}$-alkyl, CO$_2$H, CO$_2$—C$_{1-6}$-alkyl, CF$_3$, C$_{1-6}$-Alkyl; a phenyl radical bonded via a C$_{1-3}$-alkyl chain and in each case unsubstituted or mono- or polysubstituted by F, Cl, CN, NO$_2$, SH, S—C$_{1-6}$-alkyl, OH, O—C$_{1-6}$-alkyl, CO$_2$H, CO$_2$—C$_{1-6}$-alkyl, CF$_3$, C$_{1-6}$-alkyl. Particularly preferably R$^3$ denotes phenyl, unsubstituted or mono- or polysubstituted by F, Cl, OH, OCH$_3$, CF$_3$ or CH$_3$; thienyl; or a phenyl group bonded via a C$_{1-3}$-alkyl chain and unsubstituted or mono- or polysubstituted by F, Cl, CN, OH, OCH$_3$, CF$_3$ or CH$_3$. Particularly preferred cyclohexane derivatives are those in which R$^3$ denotes phenyl, unsubstituted or monosubstituted by Cl or F, phenethyl or thienyl.

Substituted amide compounds which are furthermore preferred are those in which R$^5$ represents H, CH$_3$, COOH, COOCH$_3$ or CH$_2$OH. Particularly preferred are compounds in which R$^5$ denotes H or CH$_3$.

Substituted cyclohexane derivatives which are moreover preferred are those wherein the radical R$^6$ represents H.

Preferred substituted cyclohexane compounds are moreover those of formula I in which R$^7$, R$^8$, R$^9$ and R$^{10}$ each independently denote H; C$_{1-5}$-alkyl, branched or unbranched, unsubstituted or mono- or polysubstituted; F, Cl, Br, I, CF$_3$, OH, OCH$_3$, NH$_2$, COOH, COOCH$_3$, NHCH$_3$ or N(CH$_3$)$_2$, NO$_2$ or phenyl. Preferably R$^3$ and R$^9$ each independently represent H; C$_{1-5}$-alkyl, F, Cl, Br, I, OH, OCH$_3$, COOH, COOCH$_3$, NH$_2$, NHCH$_3$, N(CH$_3$)$_2$ or NO$_2$, while R$^{10}$ and R$^7$ each denote H. Particularly preferred substituted cyclohexane derivatives are those of formula I in which R$^8$ represents H, F or CH$_3$, while R$^7$, R$^9$ and R$^{10}$ denote H.

Substituted cyclohexane derivatives are furthermore particularly preferred in which X denotes O or NR$^{17}$, wherein R$^{17}$ represents H, CH$_3$, C$_2$H$_5$, acetyl, phenyl, benzyl or COR$^{12}$. In particular R$^{17}$ represents H or COR$^{12}$. It is preferable for W to represent NH. It is furthermore preferable for R$^{12}$ to represent phenyl, phenethyl, phenethenyl, 1-methyl-phenethyl or benzyl, unsubstituted or mono- or polysubstituted by F, Cl, Br, I, CN, NH$_2$, NH—C$_{1-6}$-alkyl, NH—C$_{1-6}$-alkyl-OH, N(C$_{1-6}$-alkyl)$_2$, N(C$_{1-6}$-alkyl-OH)$_2$, NO$_2$, SH, S—C$_{1-6}$-alkyl, OH, O—C$_{1-6}$-alkyl, O—C$_{1-6}$-alkyl-OH, C(=O)C$_{1-6}$-alkyl, CO$_2$H, CO$_2$—C$_{1-6}$-alkyl, CF$_3$, C$_{1-6}$-alkyl; thienyl or benzothienyl, optionally bridged via a CH$_2$ or a CH$_2$CH$_2$ chain, unsubstituted or mono- or polysubstituted by F, Cl, Br, I, CN, NH$_2$, NH—C$_{1-6}$-alkyl, NH—C$_{1-6}$-alkyl-OH, N(C$_{1-6}$-alkyl)$_2$, N(C$_{1-6}$-alkyl -OH)$_2$, NO$_2$, SH, S—C$_{1-6}$-alkyl, OH, O—C$_{1-6}$-alkyl, O—C$_{1-6}$-alkyl-OH, C(=O)C$_{1-6}$-alkyl, CO$_2$H, CO$_2$—C$_{1-6}$-alkyl, CF$_3$, C$_{1-6}$-alkyl; or cyclopropyl, cyclobutyl, cyclopentyl or cyclohexyl, optionally bridged via a CH$_2$ or a CH$_2$CH$_2$ chain, in each case unsubstituted or mono- or polysubstituted by F, Cl, Br, —CN, NH$_2$, NH—C$_{1-6}$-alkyl, NH—C$_{1-6}$-alkyl-OH, C$_{1-6}$-alkyl, N(C$_{1-6}$-alkyl)$_2$, N(C$_{1-6}$-alkyl-OH)$_2$, NO$_2$, SH, S—C$_{1-6}$-alkyl, S-benzyl, O—C$_{1-6}$-alkyl, OH, O—C$_{1-6}$-alkyl-OH, =O, O-benzyl, C(=O)C$_{1-6}$-alkyl, CO$_2$H, CO$_2$—C$_{1-6}$-alkyl or benzyl; (CHR$^a$)$_q$OR$^{13}$, q=1 or 2 and R$^a$=H or methyl. in particular, R$^{12}$ represents phenyl, cyclohexyl, methyl-tert-butyl, 3,4-dimethoxybenzyl, 1-methyl-phenethyl, 4-chlorophenoxymethyl, 2-chloro-phenethenyl, 2-benzothienyl, methyl, phenethyl, methoxymethyl, thienylmethyl, benzyloxymethyl, ethylcyclopentyl, cyclopropyl, 2-ethyl-pentyl, 1-methyl-ethyl, ethyl, 4-fluorobenzyl, 3-chloro-2-benzothienyl, cyclopentyl, 3-methoxybenzyl, 2-phenoxyethyl, 5-methyl-2-benzothienyl, 2-methyl-propyl, phenethyl or 1-ethyl-propyl.

Particularly preferred spirocyclic cyclohexane compounds are selected from the group consisting of:

(17) 1,1-[3-(dimethylamino-(4-fluorophenyl)methyl)-pentamethylene]-3,4-dihydro-1H-2,9-diazafluorene
(18) 1,1-[3-(dimethylamino-(3-fluorophenyl)methyl)-pentamethylene]-3,4-dihydro-1H-2,9-diazafluorene
(19) 1,1-[3-(dimethylamino-phenylmethyl)-pentamethylene]-3,4-dihydro-1H-2,9-diazafluorene
(20) 1,1-[3-(dimethylamino-(phenylethyl)-methyl)-pentamethylene]-3,4-dihydro-1H-2,9-diazafluorene citrate
(21) 1,1-[3-(dimethylamino-(thiophen-2-yl)-methyl)-pentamethylene]-3,4-dihydro-1H-2,9-diazafluorene
(22) 1,1-[3-(4-chlorophenyl-(dimethylamino)-methyl)-pentamethylene]-3,4-dihydro-1H-2,9-diazafluorene
(23) cyclohexyl{1,1-[3-(dimethylamino-(4-fluorophenyl)-methyl)-pentamethylene]-3,4-dihydro-1H-2,9-diazafluoren-2-yl}methanone
(24) phenyl{1,1-[3-(dimethylamino-(4-fluorophenyl)-methyl)-pentamethylene]-3,4-dihydro-1H-2,9-diazafluoren-2-yl}methanone
(25) 1,1-[3-(dimethylamino-(4-fluorophenyl)-methyl)-pentamethylene]-1,3,4,9-tetrahydro-pyrano[3,4-b]indole
(26) 1,1-[3-(dimethylamino-(3-fluorophenyl)-methyl)-pentamethylene]-1,3,4,9-tetrahydro-pyrano[3,4-b]indole
(27) 1,1-[3-(dimethylamino-(phenyl)-methyl)-pentamethylene]-1,3,4,9-tetrahydropyrano[3,4-b]indole citrate
(28) 1,1-[3-(dimethylamino-(phenylethyl)-methyl)-pentamethylene]-1,3,4,9-tetrahydropyrano[3,4-b]indole
(29) 1,1-[3-(dimethylamino-(thiophen-2-yl)-methyl)-pentamethylene]-1,3,4,9-tetrahydro-pyrano[3,4-b]indole
(30) 1,1-[3-(dimethylamino-(4-chlorophenyl)-methyl)-pentamethylene]-1,3,4,9-tetrahydro-pyrano[3,4-b]indole
(35) 6-fluoro-1,1-[3-(dimethylamino-(4-fluorophenyl)-methyl)-pentamethylene]-1,3,4,9-tetrahydropyrano[3,4-b]indole
(36) 6-fluoro-1,1-[3-(dimethylamino-(3-fluorophenyl)-methyl)-pentamethylene]-1,3,4,9-tetrahydropyrano[3,4-b]indole
(37) 6-fluoro-1,1-[3-(dimethylamino-(phenyl)-methyl)-pentamethylene]-1,3,4,9-tetrahydro-pyrano[3,4-b]indole
(38) 6-fluoro-1,1-[3-(dimethylamino-(4-chlorophenyl)-methyl)-pentamethylene]-1,3,4,9-tetrahydropyrano[3,4-b]indole
(40) 3,6-dimethyl-1,1-[3-(dimethylamino-(4-fluorophenyl)-methyl)-pentamethylene]-1,3,4,9-tetrahydropyrano[3,4-b]indole
(41) 3,6-dimethyl-1,1-[3-(dimethylamino-(3-fluorophenyl)-methyl)-pentamethylene]-1,3,4,9-tetrahydropyrano[3,4-b]indole
(42) 3,6-dimethyl-1,1-[3-(dimethylamino-(phenyl)-methyl)-pentamethylene]-1,3,4,9-tetrahydropyrano[3,4-b]indole citrate
(43) 3,6-dimethyl-1,1-[3-(dimethylamino-(phenylethyl)-methyl)-pentamethylene]-1,3,4,9-tetrahydropyrano[3,4-b]indole
(44) 3,6-dimethyl-1,1-[3-(dimethylamino-(4-chlorophenyl)-methyl)-pentamethylene]-1,3,4,9-tetrahydropyrano[3,4-b]indole
(51) 6-fluoro-3-methyl-1,1-[3-(dimethylamino-(4-fluorophenyl)-methyl)-pentamethylene]-1,3,4,9-tetrahydropyrano[3,4-b]indole
(52) 6-fluoro-3-methyl-1,1-[3-(dimethylamino-(3-fluorophenyl)-methyl)-pentamethylene]-1,3,4,9-tetrahydropyrano[3,4-b]indole
(53) 6-fluoro-3-methyl-1,1-[3-(dimethylamino-(phenyl)-methyl)-pentamethylene]-1,3,4,9-tetrahydropyrano[3,4-b]indole

(54) 6-fluoro-3-methyl-1,1-[3-(dimethylamino-(phenyl-ethyl) -methyl)-pentamethylene]-1,3,4,9-tetrahydropyrano[3,4-b]indole
(55) 6-fluoro-3-methyl-1,1-[3-(dimethylamino-(4-chlorophenyl)-methyl)-pentamethylene]-1,3,4,9-tetrahydropyrano[3,4-b]indole
(56) 1-{1,1-[3-(dimethylamino-phenylmethyl)-pentamethylene]-3,4-dihydro-1H-2,9-diazafluoren-2-yl}-3,3-dimethylbutan-1-one
(57) 2-[(3,4-dimethoxyphenyl)acetyl]-{1,1-[3-(dimethylamino-phenylmethyl)-pentamethylene]-3,4-dihydro-1H-2,9-diazafluorene}
(58) 1-{1,1-[3-(dimethylamino-phenylmethyl)-pentamethylene]-3,4-dihydro-1H-2,9-diazafluoren-2-yl}-2-methyl-3-phenylprop-2-en-1-one
(59) 2-(cyclohexylcarbonyl)-{1,1-[3-(dimethylamino -phenylmethyl)-pentamethylene]-3,4-dihydro-1H-2,9-diazafluorene}
(60) 2-[(4-chlorophenoxy)acetyl]-{1,1-[3-(dimethylamino-phenylmethyl)-pentamethylene]-3,4-dihydro-1H-2,9-diazafluorene}
(61) 1-{1,1-[3-(dimethylamino-phenylmethyl)-pentamethylene]-3,4-dihydro-1H-2,9-diazafluoren-2-yl}-3-(2-chlorophenyl)prop-2-en-1-one
(62) 1-{1,1-[3-(dimethylamino-(4-fluorophenyl)methyl) -pentamethylene]-3,4-dihydro-1H-2,9-diazafluoren-2-yl}-3,3-dimethylbutan-1-one
(63) 2-[(3,4-dimethoxyphenyl)acetyl]-{1,1-[3-(dimethylamino-(4-fluorophenyl)methyl)-pentamethylene]-3,4-dihydro-1H-2,9-diazafluorene}
(64) 1-{1,1-[3-(dimethylamino-(4-fluorophenyl)methyl) -pentamethylene]-3,4-dihydro-1H-2,9-diazafluoren-2-yl}-2-methyl-3-phenylprop-2-en-1-one
(65) 2-[(4-chlorophenoxy)acetyl]-{1,1-[3-(dimethylamino-(4-fluorophenyl)methyl)-pentamethylene]-3,4-dihydro-1H-2,9-diazafluorene}
(66) 1-{1,1-[3-(dimethylamino-(3-fluorophenyl)methyl) -pentamethylene]-3,4-dihydro-1H-2,9-diazafluoren-2-yl}-3,3-dimethylbutan-1-one
(67) 2-[(3,4-dimethoxyphenyl)acetyl]-{1,1-[3-(dimethylamino-(3-fluorophenyl)methyl)-pentamethylene]-3,4-dihydro-1H-2,9-diazafluorene}
(68) 1-{1,1-[3-(dimethylamino-(3-fluorophenyl)methyl) -pentamethylene]-3,4-dihydro-1H-2,9-diazafluoren-2-yl}-2-methyl-3-phenylprop-2-en-1-one
(69) 2-(cyclohexylcarbonyl)-{1,1-[3-(dimethylamino-(3-fluorophenyl)methyl)-pentamethylene]-3,4-dihydro-1H-2,9-diazafluorene}
(70) 2-[(4-chlorophenoxy)acetyl]-{1,1-[3-(dimethylamino-(3-fluorophenyl)methyl)-pentamethylene]-3,4-dihydro-1H-2,9-diazafluorene}
(71) 2-(1-benzothien-2-ylcarbonyl)-{1,1-[3-(dimethylamino-(3-fluorophenyl)methyl)-pentamethylene]-3,4-dihydro-1H-2,9-diazafluorene}
(72) 1-{1,1-[3-(dimethylamino-(3-fluorophenyl)methyl) -pentamethylene]-3,4-dihydro-1H-2,9-diazafluoren-2-yl}-3-(2-chlorophenyl)prop-2-en-1-one
(73) 1-{1,1-[3-(dimethylamino-(4-chlorophenyl)methyl) -pentamethylene]-3,4-dihydro-1H-2,9-diazafluoren-2-yl}-3,3-dimethylbutan-1-one
(74) 2-[(3,4-dimethoxyphenyl)acetyl]-{1,1-[3-(dimethylamino-(4-chlorophenyl)-methyl)-pentamethylene]-3,4-dihydro-1H-2,9-diazafluorene}
(75) 1-{1,1-[3-(dimethylamino-(4-chlorophenyl)methyl) -pentamethylene]-3,4-dihydro-1H-2,9-diazafluoren-2-yl}-2-methyl-3-phenylprop-2-en-1-one
(76) 2-(cyclohexylcarbonyl)-{1,1-[3-(dimethylamino-(4-chlorophenyl)methyl)-pentamethylene]-3,4-dihydro-1H-2,9-diazafluorene}
(77) 2-[(4-chlorophenoxy)acetyl]-{1,1-[3-(dimethylamino-(4-chlorophenyl)-methyl)-pentamethylene]-3,4-dihydro-1H-2,9-diazafluorene}
(78) 2-(1-benzothien-2-ylcarbonyl)-{1,1-[3-(dimethylamino-(4-chlorophenyl)-methyl)-pentamethylene]-3,4-dihydro-1H-2,9-diazafluorene}
(79) 2-acetyl-{1,1-[3-(dimethylamino-phenylmethyl) -pentamethylene]-3,4-dihydro-1H-2,9-diazafluorene}
(80) 1-{1,1-[3-(dimethylamino-phenylmethyl)-pentamethylene]-3,4-dihydro-1H-2,9-diazafluoren-2-yl}-3-phenylprop-2-en-1-one
(81) 2-(methoxyacetyl)-{1,1-[3-(dimethylamino-phenylmethyl) -pentamethylene]-3,4-dihydro-1H-2,9-diazafluorene}
(82) 2-(2-thienylacetyl)-{1,1-[3-(dimethylamino -phenylmethyl)-pentamethylene]-3,4-dihydro-1H-2,9-diazafluorene}
(83) 2-(benzyloxyacetyl)-{1,1-[3-(dimethylamino-phenylmethyl) -pentamethylene]-3,4-dihydro-1H-2,9-diazafluorene}
(84) acetyl-{1,1-[3-(dimethylamino-(4-fluorophenyl)methyl) -pentamethylene]-3,4-dihydro-1H-2,9-diazafluorene}
(85) 2-(3-cyclopentylpropanoyl)-{1,1-[3-(dimethylamino-(4-fluorophenyl)methyl)-pentamethylene]-3,4-dihydro-1H-2,9-diazafluorene}
(86) 1-{1,1-[3-(dimethylamino-(4-fluorophenyl)methyl) -pentamethylene]-3,4-dihydro-1H-2,9-diazafluoren-2-yl}-3-phenylprop-2-en-1-one
(87) 2-(2-thienylacetyl)-{1,1-[3-(dimethylamino-(4-fluorophenyl)methyl)-pentamethylene]-3,4-dihydro-1H-2,9-diazafluorene}
(88) 2-(benzyloxyacetyl)-{1,1-[3-(dimethylamino-(4-fluorophenyl)methyl)-pentamethylene]-3,4-dihydro-1H-2,9-diazafluorene}
(89) acetyl-{1,1-[3-(dimethylamino-(3-fluorophenyl)methyl) -pentamethylene]-3,4-dihydro-1H-2,9-diazafluorene}
(90) 2-(3-cyclopentylpropanoyl)-{1,1-[3-(dimethylamino-(3-fluorophenyl)methyl)-pentamethylene]-3,4-dihydro-1H-2,9-diazafluorene}
(91) 2-(cyclopropylcarbonyl)-{1,1-[3-(dimethylamino-(3-fluorophenyl)methyl)-pentamethylene]-3,4-dihydro-1H-2,9-diazafluorene}
(92) 2-(methoxyacetyl)-{1,1-[3-(dimethylamino-(3-fluorophenyl)methyl)-pentamethylene]-3,4-dihydro-1H-2,9-diazafluorene}
(93) 2-(2-thienylacetyl)-{1,1-[3-(dimethylamino-(3-fluorophenyl)methyl)-pentamethylene]-3,4-dihydro-1H-2,9-diazafluorene}
(94) 2-(benzyloxyacetyl)-{1,1-[3-(dimethylamino-(3-fluorophenyl)methyl)-pentamethylene]-3,4-dihydro-1H-2,9-diazafluorene}
(95) 2-(3-cyclopentylpropanoyl)-{1,1-[3-(dimethylamino-(4-chlorophenyl)-methyl)-pentamethylene]-3,4-dihydro-1H-2,9-diazafluorene}
(96) 2-(cyclopropylcarbonyl)-{1,1-[3-(dimethylamino-(4-chlorophenyl)methyl)-pentamethylene]-3,4-dihydro-1H-2,9-diazafluorene}
(97) 2-(methoxyacetyl)-{1,1-[3-(dimethylamino-(4-chlorophenyl)methyl)-pentamethylene]-3,4-dihydro-1H-2,9-diazafluorene}

(98) 2-(2-thienylacetyl)-{1,1-[3-(dimethylamino-(4-chlorophenyl)methyl)-pentamethylene]-3,4-dihydro-1H-2,9-diazafluorene}
(99) 2-(benzyloxyacetyl)-{1,1-[3-(dimethylamino-(4-chlorophenyl)methyl)-pentamethylene]-3,4-dihydro-1H-2,9-diazafluorene}
(100) 2-(2-ethylhexanoyl)-{1,1-[3-(dimethylamino -phenylmethyl)-pentamethylene]-3,4-dihydro-1H-2,9-diazafluorene}
(101) 2-isobutyryl-{1,1-[3-(dimethylamino-phenylmethyl)-pentamethylene]-3,4-dihydro-1H-2,9-diazafluorene}
(102) 2-propionyl-{1,1-[3-(dimethylamino-phenylmethyl)-pentamethylene]-3,4-dihydro-1H-2,9-diazafluorene}
(103) 2-(1-benzothien-3-ylcarbonyl)-{1,1-[3-(dimethylamino-phenylmethyl)-pentamethylene]-3,4-dihydro-1H-2,9-diazafluorene}
(104) 2-[(4-fluorophenyl)acetyl]-{1,1-[3-(dimethylamino-phenylmethyl)-pentamethylene]-3,4-dihydro-1H-2,9-diazafluorene}
(105) 2-(3-chloro-1-benzothien-2-ylcarbonyl)-{1,1-[3-(dimethylamino-phenylmethyl)-pentamethylene]-3,4-dihydro-1H-2,9-diazafluorene}
(106) 2-(2-ethylhexanoyl)-{1,1-[3-(dimethylamino-(4-fluorophenyl)methyl)-pentamethylene]-3,4-dihydro-1H-2,9-diazafluorene}
(107) 2-isobutyryl-{1,1-[3-(dimethylamino-(4-fluorophenyl)methyl)-pentamethylene]-3,4-dihydro-1H-2,9-diazafluorene}
(108) 2-propionyl-{1,1-[3-(dimethylamino-(4-fluorophenyl)methyl)-pentamethylene]-3,4-dihydro-1H-2,9-diazafluorene}
(109) 2-cyclopentylcarbonyl-{1,1-[3-(dimethylamino-(4-fluorophenyl)methyl)-pentamethylene]-3,4-dihydro-1H-2,9-diazafluorene}
(110) 2-[(4-fluorophenyl)acetyl]-{1,1-[3-(dimethylamino-(4-fluorophenyl)methyl)-pentamethylene]-3,4-dihydro-1H-2,9-diazafluorene}
(111) 2-(2-ethylhexanoyl)-{1,1-[3-(dimethylamino-(3-fluorophenyl)methyl)-pentamethylene]-3,4-dihydro-1H-2,9-diazafluorene}
(112) 2-isobutyryl-{1,1-[3-(dimethylamino-(3-fluorophenyl)methyl)-pentamethylene]-3,4-dihydro-1H-2,9-diazafluorene}
(113) 2-propionyl-{1,1-[3-(dimethylamino-(3-fluorophenyl)methyl)-pentamethylene]-3,4-dihydro-1H-2,9-diazafluorene}
(114) 2-(1-benzothien-3-ylcarbonyl)-{1,1-[3-(dimethylamino-(3-fluorophenyl)methyl)-pentamethylene]-3,4-dihydro-1H-2,9-diazafluorene}
(115) 2-cyclopentylcarbonyl-{1,1-[3-(dimethylamino-(3-fluorophenyl)methyl)-pentamethylene]-3,4-dihydro-1H-2,9-diazafluorene}
(116) 2-[(4-fluorophenyl)acetyl]-{1,1-[3-(dimethylamino-(3-fluorophenyl)methyl)-pentamethylene]-3,4-dihydro-1H-2,9-diazafluorene}
(117) 2-(3-chloro-1-benzothien-2-ylcarbonyl)-{1,1-[3-(dimethylamino-(3-fluorophenyl)methyl)-pentamethylene]-3,4-dihydro-1H-2,9-diazafluorene}
(118) 2-(2-ethylhexanoyl)-{1,1-[3-(dimethylamino-(4-chlorophenyl)methyl)-pentamethylene]-3,4-dihydro-1H-2,9-diazafluorene}
(119) 2-isobutyryl-{1,1-[3-(dimethylamino-(4-chlorophenyl)methyl)-pentamethylene]-3,4-dihydro-1H-2,9-diazafluorene}
(120) 2-propionyl-{1,1-[3-(dimethylamino-(4-chlorophenyl)methyl)-pentamethylene]-3,4-dihydro-1H-2,9-diazafluorene}
(121) 2-(1-benzothien-3-ylcarbonyl)-{1,1-[3-(dimethylamino-(4-chlorophenyl)-methyl)-pentamethylene]-3,4-dihydro-1H-2,9-diazafluorene}
(122) 2-cyclopentylcarbonyl-{1,1-[3-(dimethylamino-(4-chlorophenyl)methyl)-pentamethylene]-3,4-dihydro-1H-2,9-diazafluorene}
(123) 2-[(4-fluorophenyl)acetyl]-{1,1-[3-(dimethylamino-(4-chlorophenyl)-methyl)-pentamethylene]-3,4-dihydro-1H-2,9-diazafluorene}
(124) 2-(3-chloro-1-benzothien-2-ylcarbonyl)-{1,1-[3-(dimethylamino-(4-chloro-phenyl)methyl)-pentamethylene]-3,4-dihydro-1H-2,9-diazafluorene}
(125) 2-cyclopentylcarbonyl-{1,1-[3-(dimethylamino -phenylmethyl)-pentamethylene]-3,4-dihydro-1H-2,9-diazafluorene}
(126) 2-[(3-methoxyphenyl)acetyl]-{1,1-[3-(dimethylamino-(3-fluorophenyl)methyl)-pentamethylene]-3,4-dihydro-1H-2,9-diazafluorene}
(127) 2-(2-phenoxypropanoyl)-{1,1-[3-(dimethylamino-(3-fluorophenyl)methyl)-pentamethylene]-3,4-dihydro-1H-2,9-diazafluorene}
(128) 2-[5-methylbenzothien-2-ylcarbonyl]-{1,1-[3-(dimethylamino-(3-fluorophenyl)methyl)-pentamethylene]-3,4-dihydro-1H-2,9-diazafluorene}
(129) 1-{1,1-[3-(dimethylamino-(3-fluorophenyl)methyl)-pentamethylene]-3,4-dihydro-1H-2,9-diazafluoren-2-yl}-3-methylbutan-1-one
(130) 1-{1,1-[3-(dimethylamino-(3-fluorophenyl)methyl)-pentamethylene]-3,4-dihydro-1H-2,9-diazafluoren-2-yl}-3-phenylbutan-1-one
(131) 2-(3-phenylpropanoyl)-{1,1-[3-(dimethylamino-(4-chlorophenyl)methyl)-pentamethylene]-3,4-dihydro-1H-2,9-diazafluorene}
(132) 2-[(3-bromophenyl)acetyl]-{1,1-[3-(dimethylamino-(4-chlorophenyl)-methyl)-pentamethylene]-3,4-dihydro-1H-2,9-diazafluorene}
(133) 2-(2-phenoxypropanoyl)-{1,1-[3-(dimethylamino-(4-chlorophenyl)methyl)-pentamethylene]-3,4-dihydro-1H-2,9-diazafluorene}
(134) 1-{1,1-[3-(dimethylamino-(4-chlorophenyl)methyl)-pentamethylene]-3,4-dihydro-1H-2,9-diazafluoren-2-yl}-3-methylbutan-1-one
(135) (3-phenylpropanoyl)-1-{1,1-[3-(dimethylamino-(4-chlorophenyl)methyl)-pentamethylene]-3,4-dihydro-1H-2,9-diazafluorene}
(136) 2-[(3-methoxyphenyl)acetyl]-{1,1-[3-(dimethylamino-phenylmethyl)-pentamethylene]-3,4-dihydro-1H-2,9-diazafluorene}
(137) 2-(2-phenoxypropanoyl)-{1,1-[3-(dimethylamino -phenylmethyl)-pentamethylene]-3,4-dihydro-1H-2,9-diazafluorene}
(138) 1-{1,1-[3-(dimethylamino-phenylmethyl)-pentamethylene]-3,4-dihydro-1H-2,9-diazafluoren-2-yl}-3-methylbutan-1-one
(139) 1-{1,1-[3-(dimethylamino-(4-fluorophenyl)methyl)-pentamethylene]-3,4-dihydro-1H-2,9-diazafluoren-2-yl}-2-ethylbutan-1-one
(140) 2-[(3-methoxyphenyl)acetyl]-{1,1-[3-(dimethylamino-(4-fluorophenyl)methyl)-pentamethylene]-3,4-dihydro-1H-2,9-diazafluorene}
(141) 2-(2-phenoxypropanoyl)-{1,1-[3-(dimethylamino-(4-fluorophenyl)methyl)-pentamethylene]-3,4-dihydro-1H-2,9-diazafluorene}
(142) 1-{1,1-[3-(dimethylamino-(4-fluorophenyl)methyl)-pentamethylene]-3,4-dihydro-1H-2,9-diazafluoren-2-yl}-3-phenylbutan-1-one in the form of the racemate; of the enantiomers, diastereomers, mixtures of the enantiomers or diastereomers or of an individual enantiomer or diastereomer; of the bases and/or salts of physiologically acceptable acids.

The invention also provides a process for the preparation of a spirocyclic cyclohexane compounds according to the invention. The compounds of the invention can be prepared in accordance with the following synthesis equation:

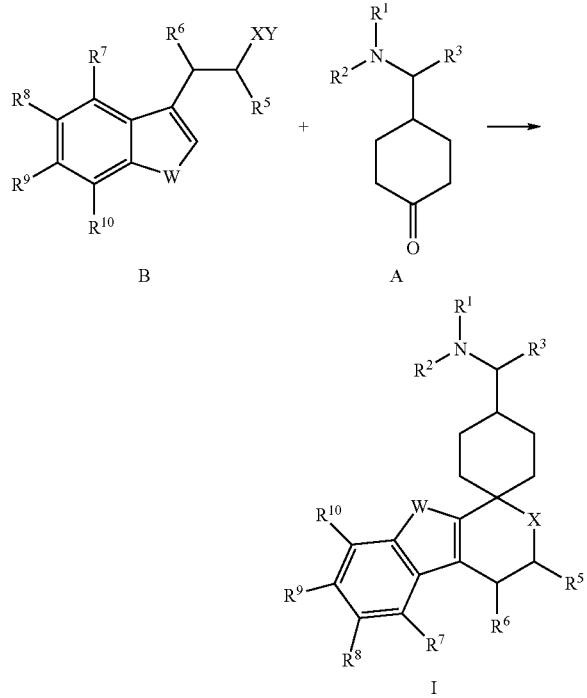

wherein Y denotes H or trimethylsilyl.

In order to prepare the compounds of formula I, ketones of formula A are reacted with heteroaromatic compounds of formula B with the addition of an acid or trimethylsilyl ester thereof, for example trifluoromethanesulfonic acid trimethylsilyl ester, acetic acid, phosphoric acid, methanesulfonic acid or trifluoroacetic, in a suitable solvent, for example dichloroethane, methylene chloride, chloroform, acetonitrile, diethyl ether or nitromethane.

In order to prepare the ketones of formula A, the keto function of 4-oxo-cyclohexanecarboxylic acid esters corresponding to the following formula:

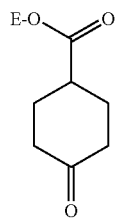

wherein E represents a $C_{1-6}$-alkyl group, preferably ethyl, is protected by methods known to persons skilled in the art to yield a compound of the formula C:

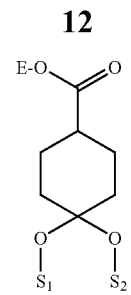

wherein $S^1$ and $S^2$ each represent a protective group. Preferably $S^1$ and $S^2$ together form a ring and represent —$CH_2$—$CH_2$—. The ester C is reduced with a reducing agent, for example diisobutylaluminium hydride, to give the aldehyde D

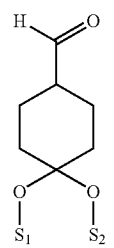

By addition of an amine of formula $R^3R^4NH$ and a cyanide, for example KCN or NaCN, the aldehyde D is converted, with the addition of an acid, for example hydrochloric acid, in an organic solvent, for example methanol or ethanol, into the nitrile E.

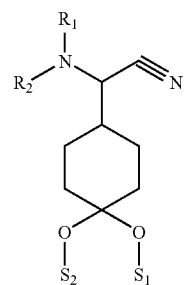

The nitrile E is reacted with a Grignard reagent of formula $R^2MgHal$, wherein Hal represents Br, Cl or I, or an organometallic compound of formula $R^2Li$ in an organic solvent, for example diethyl ether, dioxane or tetrahydrofuran, to give a compound of formula F.

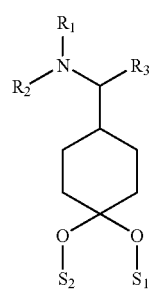

The protective groups are split off by conventional methods to yield the ketone A:

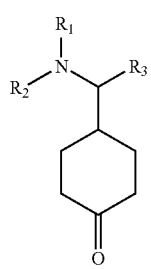

A

The compounds of formula B are either commercially obtainable, or their preparation is known from the prior art or they can be prepared analogously to synthesis processes known in the prior art as evidenced, in particular, by the following references: Jirkovsky et al., J. Heterocycl. Chem., 12, 1975, 937-940; Campaigne et al., J. Heterocycl. Chem., 2, 1965, 231-235; Efange et al., J. Med. Chem., 41, 1998, 4486-4491; Ellingboe et al., J. Med. Chem., 35, 1992, 1176-1183; Pearson et al., Aust. J. Chem., 44, 1991, 907-917; Yokohama et al., Chem. Pharm. Bull., 40, 1992, 2391-2398; Beck et al., J. Chem. Soc. Perkin 1, 1992, 813-822; Shinada et al., Tetrahedron Lett., 39, 1996, 7099-7102; Garden et al., Tetrahedron, 58, 2002, 8399-8412.

The diastereomers optionally obtained during the syntheses can be separated by methods known to persons skilled in the art for separation of diastereomers, e.g. by chromatography, in particular on silica gel, normal phase or reverse phase. RP-HPLC (mobile phase acetonitrile/water or methanol/water) is particularly suitable for separation of the diastereomers.

Spirocyclic cyclohexane compounds corresponding to formula I in which X denotes $NR^{17}$ and $R^{17}$ denotes $COR^{12}$ or $SO_2R^{12}$ can be obtained by reacting spirocyclic cyclohexane compounds corresponding to formula I in which X denotes NH, with an anhydride or an acid chloride with the addition of a base, for example triethylamine. This reaction preferably takes place under microwave irradiation.

Spirocyclic cyclohexane compounds corresponding to formula I in which X denotes SO or $SO_2$ can be obtained by reaction of spirocyclic cyclohexane compounds corresponding to formula I in which X denotes S with an oxidizing agent, for example $H_2O_2$.

It has been found that the compounds according to the invention not only bind to the µ opioid receptor, but also inhibit the reuptake of serotonin and noradrenaline. Noradrenaline and serotonin reuptake inhibitors have an antidepressant and anxiolytic action, but are also suitable for treatment of pain (see: Analgesics—from Chemistry and Pharmacology to Clinical Application, Wiley 2002, p. 265-284).

The compounds according to the invention are suitable as active compounds in pharmaceutical compositions. The invention therefore also provides pharmaceutical compositions containing at least one substituted spirocyclic cyclohexane derivative according to the invention and optionally suitable additives and/or auxiliary substances and/or optionally further active compounds.

The pharmaceutical compositions according to the invention optionally contain, in addition to at least one substituted spirocyclic cyclohexane derivative according to the invention, suitable additives and/or auxiliary substances, that is to say also carrier materials, fillers, solvents, diluents, dyestuffs and/or binders, and can be administered as liquid medicament forms in the form of injection solutions, drops or juices, or as semi-solid medicament forms in the form of granules, tablets, pellets, patches, capsules, plasters or aerosols. The choice of auxiliary substances etc. and the amounts thereof to be employed depend on whether the medicament is to be administered orally, perorally, parenterally, intravenously, intraperitoneally, intradermally, intramuscularly, intranasally, buccally, rectally or locally, for example on the skin, the mucous membranes or into the eyes. Formulations in the form of tablets, coated tablets, capsules, granules, drops, juices and syrups are suitable for oral administration, and solutions, suspensions, easily reconstitutable dry formulations and sprays are suitable for parenteral, topical and inhalatory administration. Spirocyclic cyclohexane derivatives according to the invention in a depot, in dissolved form or in a plaster, optionally with the addition of agents which promote penetration through the skin, are suitable formulations for percutaneous administration. Formulation forms which can be used orally or percutaneously can release the spirocyclic cyclohexane derivatives according to the invention in a delayed manner. In principle, other further active compounds known to the person skilled in the art can be added to the pharmaceutical compositions according to the invention.

The amount of active compound to be administered to patients varies as a function of the weight of the patient, of the mode of administration, the indication and the severity of the disease. 0.005 to 20 mg/kg, preferably 0.05 to 5 mg/kg of at least one spirocyclic cyclohexane derivative according to the invention are usually administered.

The pharmaceutical composition can contain a spirocyclic cyclohexane compound according to the invention as the pure diastereomer and/or enantiomer, as a racemate or as a nonequimolar or equimolar mixture of the diastereomers and/or enantiomers.

The invention also provides for the use of a spirocyclic cyclohexane compound according to the invention for the treatment of pain, in particular acute, neuropathic or chronic pain.

The invention additionally provides for the use of a spirocyclic cyclohexane compound according to the invention for the treatment of depression and/or for anxiolysis.

The substituted spirocyclic cyclohexane compounds corresponding to formula I are also suitable for treatment of urinary incontinence, diarrhea, pruritus, alcohol and drug abuse, medicament dependency and lethargy.

EXAMPLES

Synthesis of Ketones 11-16

Ketones 11-16 were prepared in a five-stage synthesis from 4-oxo-cyclohexanecarboxylic acid ethyl ester.

1,4-Dioxa-spiro[4.5]decane-8-carboxylic Acid Ethyl Ester 2

4-Oxo-cyclohexanecarboxylic acid ethyl ester 1 (52.8 g, 0.31 mol, Merck, order no. 814249), ethylene glycol (67.4 g, 1.08 mol) and p-toluenesulfonic acid (0.7 g) in toluene (160 ml) were stirred at RT for 20 hours. The reaction solution was poured into diethyl ether (300 ml), and the mixture was washed with water, sodium bicarbonate solution and sodium chloride solution. The solution was dried ($Na_2SO_4$), concentrated i. vac. and the colorless liquid which remained was processed further without purification.

Yield: 66.5 g (100%)

$^1$H-NMR ($CDCl_3$): 1.24 (t, 3 H); 1.53 (m, 2 H); 1.76 (m, 4 H); 1.92 (m, 2 H); 2.31 (m, 1 H); 3.91 (s, 4 H); 4.11 (q, 2 H).

$^{13}$C-NMR (CDCl$_3$): 14.28 (q); 26.32 (t); 33.76 (t); 41.59 (d); 60.14 (t); 64.21 (t); 107.90 (d); 174.77 (s).

1,4-Dioxa-spiro[4.5]decane-8-carbaldehyde 3

Diisobutylaluminium hydride (1.5 M solution in toluene, 102 ml, 153 mmol) was added dropwise to a solution of 1,4-dioxa-spiro[4.5]decane-8-carboxylic acid ethyl ester 2 (32.13 g, 150 mmol) in absol. toluene (160 mol) at −70 to −65° C. under argon and the mixture was stirred for 30 min. The mixture was then quenched at −70 to −60° C. by addition of methanol (80 ml). The reaction solution was warmed to RT, saturated sodium chloride solution (100 ml) was added, and the reaction solution was filtered with suction over kieselguhr. The kieselguhr was washed twice with ethyl acetate, and the aqueous solution was separated and extracted twice with ethyl acetate. The combined organic extracts were washed with saturated sodium chloride solution, dried over sodium sulfate and concentrated under reduced pressure.
Yield: 24.01 g (94%), yellow oil
$^1$H-NMR (CDCl$_3$): 1.54 (m, 2 H); 1.74 (m, 4 H); 1.91 (m, 2 H); 2.21 (m, 1 H); 3.91 (s, 4 H); 9.60 (s, 1 H).
$^{13}$C-NMR (CDCl$_3$): 23.35 (t); 33.37 (t); 48.18 (d); 64.30 (t); 107.89 (d); 203.51 (s).

Dimethylamino-(1,4-dioxa-spiro[4.5]dec-8-yl)-acetonitrile 4

40 percent strength aqueous dimethylamine solution (85 ml, 0.67 mol), 1,4-dioxa-spiro[4.5]decane-8-carbaldehyde 3 (240 g, 0.141 mol) and potassium cyanide (22.05 g, 0.338 mol) were added to a mixture of 4 N hydrochloric acid (37 ml) and methanol (22 ml), while cooling with ice. The mixture was stirred at room temperature for 4 d and then, after addition of water (80 ml), extracted with diethyl ether (4×100 ml). The organic phase was dried over sodium sulfate and concentrated i. vac. and the product was obtained as a white solid.
Yield: 25.2 g (81%)
Melting point: 48-51° C.
$^1$H-NMR (CDCl$_3$): 1.23-2.03 (m, 9 H); 2.28 (s, 6 H); 3.16 (d, 1 H); 3.93 (m, 4H).
$^{13}$C-NMR (CDCl$_3$): 26.67 (t); 27.93 (t); 33.87 (t); 36.94 (d); 41.90 (q); 64.30 (t); 64.36 (t); 108.33 (d); 115.94 (s).

[(1,4-Dioxa-spiro[4.5]dec-8-yl)-4-fluorophenyl-methyl]-dimethylamine 5 (R$^3$=4-fluorophenyl)

A solution of the aminonitrile 4 (19.89 g, 88 mmol) in absol. THF (160 ml) was added dropwise to a 1 M solution of 4-fluorophenylmagnesium bromide in THF (220 ml, 220 mmol) under argon and while cooling with ice and the mixture was stirred at RT for 20 h. The reaction mixture was worked up by adding saturated ammonium chloride solution (100 ml) and water (100 ml) while cooling with ice, and extracting the mixture with diethyl ether (3×100 ml). The organic phase was washed with water and saturated sodium chloride solution, dried (Na$_2$SO$_4$) and concentrated.
Yield: 31 g (>100%)
$^{13}$C-NMR (CDCl$_3$): 26.68 (t); 28.11 (t); 34.43 (t); 34.55 (t); 37.37 (d); 41.68 (q); 64.12 (t); 73.65 (d); 108.88 (d); 114.23 (d); 114.44 (d); 130.27; 130.35; 132.43; 160.36 (s); 162.78 (s).

[(1,4-Dioxa-spiro[4.5]dec-8-yl)-3-fluorophenyl-methyl]-dimethylamine 6 (R$^3$=3-fluorophenyl)

A solution of the aminonitrile 4 (23.45 g, 104 mmol) in absol. THF (100 ml) was added dropwise to a 1 M solution of 3-fluorophenylmagnesium bromide in THF (208 ml, 208 mmol) under argon and while cooling with ice, and the mixture was stirred at RT for 20 hours. The reaction mixture was worked up by adding saturated ammonium chloride solution (100 ml) and water (100 ml) while cooling with ice, and extracting the mixture with diethyl ether (3×100 ml). The organic phase was washed with water and saturated sodium chloride solution, dried and concentrated.
Yield: 30.33 g (99%).
$^1$H-NMR (CDCl$_3$): 1.12 (m, 1 H); 1.26 (m, 1 H); 1.46-1.81 (m, 7 H); 2.10 (s, 6H); 3.10 (d, 1 H); 3.90 (m, 4 H); 6.85 (m, 3 H); 7.27 (m, 1 H).
$^{13}$C-NMR (CDCl$_3$): 26.80 (t); 28.08 (t); 34.48 (t); 34.45 (t); 34.59 (t); 37.26 (d); 41.71 (q); 64.19 (t); 74.04 (t); 108.91 (d); 113.51 (d); 113.71 (d); 115.52 (d); 115.72 (d); 124.83 (d); 128.82 (d); 128.90 (d); 139.66 (s); 161.15 (s); 163.58 (s).

[(1,4-Dioxa-spiro[4.5]dec-8-yl)-phenyl-methyl]-dimethyl-amine 7 (R$^3$=phenyl)

A solution of the aminonitrile 4 (23.56 g, 105 mmol) in absol. THF (100 ml) was added dropwise to a 25 percent strength solution of phenylmagnesium chloride (144 ml, 262.5 mmol) in THF under argon and while cooling with ice, and the mixture was stirred at RT for 20 hours. The reaction mixture was worked up by adding saturated ammonium chloride solution (100 ml) and water (100 ml) while cooling with ice, and extracting the mixture with diethyl ether (3×100 ml). The organic phase was washed with water and saturated sodium chloride solution, dried (Na$_2$SO$_4$) and concentrated.
Yield: 28.9 g (100%).
$^{13}$C-NMR (CDCl$_3$): 27.05; 28.13; 34.48, 34.57; 36.94 (s); 41.64 (q); 64.15 (d); 74.33 (d); 109.02 (s); 126.70 (s); 127.49 (s); 129.12 (s); 136.57 (s).

[1-(1,4-Dioxa-spiro[4.5]dec-8-yl)-3-phenyl-propyl]-dimethylamine 8 (R$^3$=phenethyl)

A solution of the aminonitrile 4 (21.93 g, 97 mmol) in absol. THF (180 ml) was added dropwise to a 1 M solution of phenylethylmagnesium chloride in THF (242 ml, 242 mmol) under argon and while cooling with ice, and the mixture was stirred at RT for 20 hours. The reaction mixture was worked up by adding saturated ammonium chloride solution (100 ml) and water (100 ml) while cooling with ice, and extracting the mixture with diethyl ether (3×100 ml). The organic phase was washed with water and saturated sodium chloride solution, dried and concentrated.
Yield: 34 g (>100%).
$^{13}$C-NMR (CDCl$_3$): 27.43 (t); 28.95 (t); 29.42 (t); 34.82 (t); 35.40 (t); 38.76 (d); 41.16 (q); 64.17 (t); 67.41 (d); 108.86 (s); 125.41 (d); 127.66 (d); 128.11 (d); 142.69 (s).

[(1,4-Dioxa-spiro[4.5]dec-8-yl)-thiophen-2-yl-methyl]-dimethylamine 9 (R$^3$=2-thiophene)

A solution of the aminonitrile 4 (2.24 g, 10 mmol) in absolute THF (10 ml) was added dropwise to a 1 M solution of thiophen-2-yl-magnesium bromide in THF (20 ml, 20 mmol) under argon and while cooling with ice, and the mixture was stirred at RT for 20 hours. The reaction mixture was worked up by adding saturated ammonium chloride solution (10 ml) and water (10 ml) while cooling with ice, and extracting the mixture with diethyl ether (3×10 ml). The organic phase was washed with water and saturated sodium chloride solution, dried and concentrated.
Yield: 2.8 g (100%)

$^{13}$C-NMR (CDCl$_3$): 27.72; 27.88; 34.27; 39.28; 41.10; 64.11; 68.89; 108.88; 123.55; 125.88; 127.53; 139.50.

[(4-Chlorophenyl)-(1,4-dioxa-spiro[4.5]dec-8-yl)-methyl]-dimethylamine 10 (R$^3$=4-chlorophenyl)

A solution of the aminonitrile 4 (22.43 g, 100 mmol) in absolute ether (100 ml) was added dropwise to a 1 M solution of 4-chlorophenylmagnesium bromide in ether (200 ml, 200 mmol) under argon and while cooling with ice, and the mixture was stirred at RT for 20 hours. The reaction mixture was worked up by adding saturated ammonium chloride solution (100 ml) and water (100 ml) while cooling with ice, and extracting the mixture with diethyl ether (3×100 ml). The organic phase was washed with water and saturated sodium chloride solution, dried and concentrated.

Yield: 30.9 g (100%)

$^{13}$C-NMR (CDCl$_3$): 26.65; 28.11; 34.46; 34.60; 37.28; 41.76; 64.17; 73.80; 108.88; 127.72; 129.53; 132.39; 135.33.

4-[Dimethylamino-(4-fluorophenyl)-methyl]-cyclohexanone 11 (R$^3$=4-fluorophenyl)

The crude product of the ketal 5 (26 g, 88 mmol) was dissolved in water (40 ml), concentrated hydrochloric acid (59 ml) was added, and the mixture was stirred at RT for 20 hours. The reaction mixture was extracted with diethyl ether (2×100 ml), the aqueous phase was rendered alkaline with 5 N NaOH, while cooling with ice, the mixture was extracted with methylene chloride (3×100 ml), and the product phase was dried and concentrated.

Yield: 21.36 g (98%)

$^{13}$C-NMR (CDCl$_3$): 28.90 (t); 30.48 (t); 37.00 (t); 40.49 (t); 40.72 (t); 41.79 (q); 72.98 (d); 114.42 (d); 114.62 (d); 130.20 (d); 130.28 (d); 131.88 (s); 160.50 (s); 162.93 (s); 211.44 (s).

4-[Dimethylamino-(3-fluorophenyl)-methyl]-cyclohexanone 12 (R$^3$=3-fluorophenyl)

The ketal 6 (30.3 g, 103 mmol) was dissolved in water (44 ml), concentrated hydrochloric acid (64 ml) was added, and the mixture was stirred at RT for 20 hours. The reaction mixture was extracted by shaking with diethyl ether (2×100 ml), the aqueous phase was rendered alkaline with 5 N NaOH while cooling with ice, the mixture was extracted with methylene chloride (3×100 ml), and the product phase was dried and concentrated. The ketone was isolated as a colorless solid.

Yield: 22.4 g (87%)

Melting point: 72-75° C.

$^{13}$C-NMR (CDCl$_3$): 28.97 (t); 30.44 (t); 36.90 (t); 40.52 (t); 40.75 (t); 41.82 (q); 73.37 (d); 113.84; 114.06; 115.42; 115.62; 124.71; 129.03; 129.11; 139.00; 139.06; 161.16; 163.60; 211.40 (s).

4-(Dimethylamino-phenyl-methyl)-cyclohexanone 13 (R$^3$=phenyl)

The ketal 7 (28.9 g, 0.105 mmol) was dissolved in water (44 ml), concentrated hydrochloric acid (64 ml) was added, and the mixture was stirred at RT for 20 hours. The reaction mixture was extracted by shaking with diethyl ether (2×100 ml), the aqueous phase was rendered alkaline with 5 N NaOH, while cooling with ice, the mixture was extracted with methylene chloride (3×100 ml), and the product phase was dried and concentrated. The ketone was isolated as a colorless oil.

Yield: 18.2 g (75%)

$^1$H-NMR (CDCl$_3$): 1.20 (1 H, m); 1.33 (1 H, m); 1.74 (1 H, m); 2.17 (6 H, s, N(CH$_3$)$_2$); 2.70 (6 H, m); 3.10 (1 H, d, C$_8$—H); 7.07 (2 H, m, C$_{arom}$—H); 7.23 (3 H, m, C$_{arom}$—H).

$^{13}$C-NMR (CDCl$_3$): 29.13 (t); 30.56 (t); 36.90 (d); 40.61 (t); 40.82 (t); 41.89 (q); 73.79 (d); 127.05 (d); 127.67 (d); 129.00 (d); 136.13 (s); 211.79 (s).

4-(1-Dimethylamino-3-phenyl-propyl)-cyclohexanone 14 (R$^3$=phenethyl)

The crude product of the ketal 8 (29.6 g, 97 mmol) was dissolved in water (44 ml), conc. hydrochloric acid (64 ml) was added and the mixture was stirred at RT for 20 h. The reaction mixture was extracted by shaking with diethyl ether (2×100 ml), the aqueous phase was rendered alkaline with 5 N NaOH, while cooling with ice, the mixture was extracted with methylene chloride (3×100 ml), and the product phase was dried and concentrated. The ketone was isolated as a colorless oil.

Yield: 16.9 g (58%)

$^{13}$C-NMR (CDCl$_3$): 29.40 (t); 30.02 (t); 30.97 (t); 35.34 (t); 38.71 (t); 40.79 (t); 41.01 (t); 41.23 (q); 66.65 (d); 125.66 (d); 128.12 (d); 128.19 (d); 142.27 (s); 211.70 (s).

4-(Dimethylamino-thiophen-2-yl-methyl)-cyclohexanone 15 (R$^3$=2-thiophene)

The ketal 9 (2.80 g, 10 mmol) was dissolved in water (4.4 ml), concentrated hydrochloric acid (6.4 ml) was added, and the mixture was stirred at RT for 20 hours. The reaction mixture was extracted by shaking with diethyl ether (2×10 ml), the aqueous phase was rendered alkaline with 5 N NaOH, while cooling with ice, the mixture was extracted with methylene chloride (3×10 ml), and the product phase was dried and concentrated. The ketone was isolated as an oil.

Yield: 1.79 g (75%)

$^{13}$C-NMR (CDCl$_3$): 30.02; 30.18; 38.84; 40.29; 39.28; 41.17; 68.24; 123.88; 126.01; 126.34; 138.77; 211.49.

4-[(4-Chloro-phenyl)-dimethylamino-methyl]-cyclohexanone (R$^3$=4-chlorophenyl)

The ketal 10 (30.98 g, 100 mmol) was dissolved in water (44 ml), concentrated hydrochloric acid (64 ml) was added, and the mixture was stirred at RT for 20 hours. The reaction mixture was extracted by shaking with diethyl ether (2×100 ml), the aqueous phase was rendered alkaline with 5 N NaOH, while cooling with ice, the mixture was extracted with methylene chloride (3×100 ml), and the product phase was dried and concentrated. The ketone was isolated as an oil.

Yield: 21.9 g (82%)

$^{13}$C-NMR (CDCl$_3$): 28.88; 30.45; 36.89; 40.49; 40.74; 41.83; 73.12; 127.87; 130.16; 132.75; 134.70; 211.35.

Synthesis of the 1,1-[3-(dimethylaminoarylmethyl)-pentamethylene]-3,4-dihydro-1H-2,9-diazafluorene Derivatives

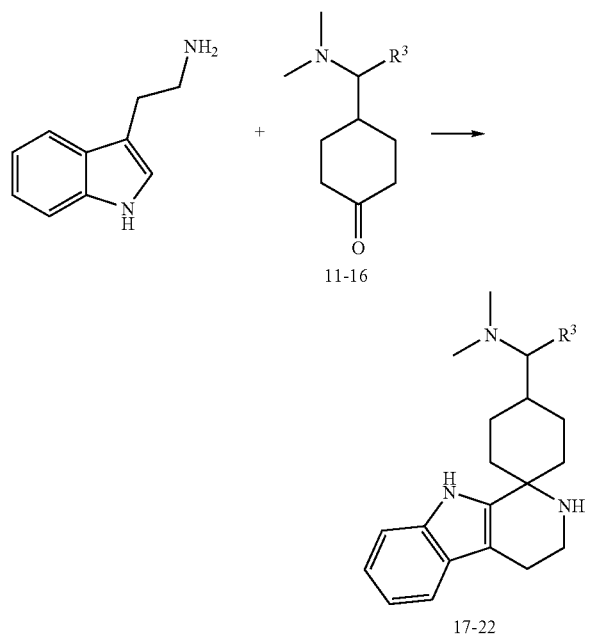

1,1-[3-(Dimethylamino-(4-fluorophenyl)methyl)-pentamethylene]-3,4-dihydro-1H-2,9-diazafluorene ($R^3$=4-fluorophenyl) 17

The ketone 11 (250 mg, 1.0 mmol) and tryptamine (161 mg, 1.0 mmol, Acros, order no. 18612) were dissolved in MeOH (10 ml), and the solution was stirred at RT overnight. The reaction solution was concentrated under reduced pressure, the residue was taken up in dichloroethane (10 ml), TFA (1 ml) was added, and the mixture was stirred at RT for 3 hours. After addition of 1 N NaOH (5 ml) and $CH_2Cl_2$ (20 ml), the mixture was subsequently stirred for a further 30 min, the phases were separated, the aqueous phase was extracted twice with $CH_2Cl_2$, and the combined organic phases were washed with water, dried ($Na_2SO_4$) and concentrated under reduced pressure. The oil which remained was dissolved in EtOH (5 ml), and the spiro compound crystallized out in a refrigerator overnight.

Yield: 260 mg (62%)
Melting point: 120-130° C.
$^{13}$C-NMR (CDCl$_3$): 23.19; 24.69; 25.86; 36.50; 36.79; 38.39; 39.26; 41.58; 52.24; 74.30; 108.33; 110.49; 114.34; 114.55; 118.04; 119.20; 121.34; 127.44; 130.40; 132.34; 135.26; 140.59; 160.45; 162.87.

1,1-[3-(Dimethylamino-(3-fluorophenyl)methyl)-pentamethylene]-3,4-dihydro-1H-2,9-diazafluorene ($R^3$=3-fluorophenyl) 18

The ketone 12 (249 mg, 1 mmol) and tryptamine (160 mg, 1 mmol, Acros, order no. 18612) were dissolved in MeOH (10 ml), and the solution was stirred at RT overnight. The reaction solution was concentrated under reduced pressure, the residue was taken up in dichloroethane (10 ml), TFA (1 ml) was added, and the mixture was stirred at RT for 2 hours. After addition of 1 N NaOH (5 ml) and $CH_2Cl_2$ (20 ml), the mixture was subsequently stirred for a further 30 min, the phases were separated, the aqueous phase was extracted twice with $CH_2Cl_2$, and the combined organic phases were washed with water, dried ($Na_2SO_4$) and concentrated under reduced pressure. The residue which remained was recrystallized from ethyl acetate/hexane.

Yield: 170 mg (43%)
Melting point: 226-229° C.
$^{13}$C-NMR (DMSO-d$_6$): 23.77; 24.23; 32.97; 33.19; 35.89; 38.14; 40.78; 57.02; 72.79; 104.87; 111.12; 113.74; 115.15; 115.35; 117.87; 118.70; 121.52; 124.95; 125.46; 129.45; 134.77; 135.72; 138.35; 158.02; 160.49; 162.89.

1,1-[3-(Dimethylamino-phenylmethyl)-pentamethylene]-3,4-dihydro-1H-2,9-diazafluorene ($R^3$=phenyl) 19

The ketone 13 (1.15 g, 5 mmol) and tryptamine (0.80 g, 5 mmol, Acros, order no. 18612) were dissolved in MeOH (50 ml), and the solution was stirred at RT overnight. The reaction solution was concentrated under reduced pressure, the residue was taken up in dichloroethane (20 ml), TFA (5 ml) was added, and the mixture was stirred at RT for 2 hours. After addition of 1 N NaOH (5 ml) and $CH_2Cl_2$ (20 ml), the mixture was subsequently stirred for a further 30 min, the phases were separated, the aqueous phase was extracted twice with $CH_2Cl_2$, and the combined organic phases were washed with water, dried ($Na_2SO_4$) and concentrated under reduced pressure. The residue which remained was recrystallized from ethyl acetate/hexane and then purified by flash chromatography with MeCN/MeOH/0.5 M NH$_4$Cl (9:1:1).

Yield: 0.84 g (45%), 1 diastereomer
Melting point: 182-184° C.
$^{13}$C-NMR (CDCl$_3$): 23.17; 24.92; 25.84; 36.48; 36.76; 38.14; 39.24; 41.53; 52.24; 74.96; 108.24; 110.48; 118.00; 119.14; 121.27; 126.75; 127.43; 127.55; 129.20; 135.24; 136.44; 140.68.

1,1-[3-(Dimethylamino-(phenylethyl)-methyl)-pentamethylene]-3,4-dihydro-1H-2,9-diazafluorene Citrate ($R^3$=phenethyl) 20

The ketone 14 (259 mg, 1.0 mmol) and tryptamine (161 mg, 1.0 mmol, Acros, order no. 18612) were dissolved in MeOH (10 ml), and the solution was stirred at RT overnight. The reaction solution was concentrated under reduced pressure, the residue was taken up in dichloroethane (10 ml), TFA (1 ml) was added, and the mixture was stirred at RT for 3 hours. After addition of 1 N NaOH (5 ml) and $CH_2Cl_2$ (20 ml), the mixture was subsequently stirred for a further 30 min, the phases were separated, the aqueous phase was extracted twice with $CH_2Cl_2$, and the combined organic phases were washed with water, dried ($Na_2SO_4$) and concentrated under reduced pressure. The oil which remained was dissolved in EtOH (5 ml), 1.5 M citric acid in EtOH (1 ml) was added, and the mixture was concentrated under reduced pressure. The spiro compound crystallized when kneaded thoroughly with acetonitrile.

Yield: 458 mg (77%)
Melting point: 130-135° C.
$^{13}$C-NMR (CDCl$_3$): 23.25; 25.22; 26.31; 29.41; 35.38; 35.46; 36.40; 36.96; 39.32; 39.84; 40.84; 41.06; 41.22; 52.09; 68.11; 108.26; 110.52; 111.03; 118.00; 119.15; 121.29; 125.57; 127.44; 128.17; 128.23; 128.43; 128.87; 135.26; 140.69; 142.73.

1,1-[3-(Dimethylamino-(thiophen-2-yl)-methyl)-pentamethylene]-3,4-dihydro-1H-2,9-diazafluorene ($R^3$=2-thiophene) 21

The ketone 15 (474 mg, 2 mmol) and tryptamine (320 mg, 2 mmol, Acros, order no. 18612) were dissolved in MeOH (20 ml), and the solution was stirred at RT overnight. The reaction solution was concentrated under reduced pressure, the residue was taken up in dichloroethane (10 ml), TFA (2 ml) was added, and the mixture was stirred at RT for 4 hours. After addition of 1 N NaOH (5 ml) and $CH_2Cl_2$ (20 ml), the mixture was subsequently stirred for a further 30 min, the phases were separated, the aqueous phase was extracted twice with $CH_2Cl_2$, and the combined organic phases were washed with water, dried ($Na_2SO_4$) and concentrated under reduced pressure. The oil which remained was dissolved in EtOH (5 ml), and the spiro compound crystallized out in a refrigerator overnight.

Yield: 258 mg (27%)
Melting point: 167-168° C.
$^{13}$C-NMR ($CDCl_3$): 23.19; 25.60; 25.71; 36.43; 36.62; 39.26; 40.56; 41.08; 52.20; 69.78; 108.24; 110.50; 118.00; 119.15; 121.30; 123.73; 126.00; 126.46; 127.40; 135.25; 139.51; 140.61.

1,1-[3-(4-Chlorophenyl-(dimethylamino)-methyl)-pentamethylene]-3,4-dihydro-1H-2,9-diazafluorene ($R^3$=4-chlorophenyl) 22

The ketone 16 (264 mg, 1 mmol) and tryptamine (161 mg, 1 mmol, Acros, order no. 18612) were dissolved in MeOH (10 ml), and the solution was stirred at RT overnight. The reaction solution was concentrated under reduced pressure, the residue was taken up in dichloroethane (10 ml), TFA (1 ml) was added, and the mixture was stirred at RT for 3 hours. After addition of 1 N NaOH (5 ml) and $CH_2Cl_2$ (20 ml), the mixture was subsequently stirred for a further 30 min, the phases were separated, the aqueous phase was extracted twice with $CH_2Cl_2$, and the combined organic phases were washed with water, dried ($Na_2SO_4$) and concentrated under reduced pressure. The oil which remained was dissolved in EtOH (5 ml), and the spiro compound crystallized out in a refrigerator overnight.

Yield: 191 mg (47%)
Melting point: 102-104° C.
$^{13}$C-NMR ($CDCl_3$): 23.18; 24.62; 25.79; 36.46; 36.76; 38.26; 39.25; 41.59; 52.22; 74.39; 108.32; 110.48; 118.02; 119.18; 121.33; 127.42; 127.78; 130.36; 132.45; 135.15; 135.25; 140.55.

Synthesis of the {1,1-[3-(dimethylamino-(4-fluorophenyl)-methyl)-pentamethylene]-3,4-dihydro-1H-2,9-diazafluoren-2-yl}methanones

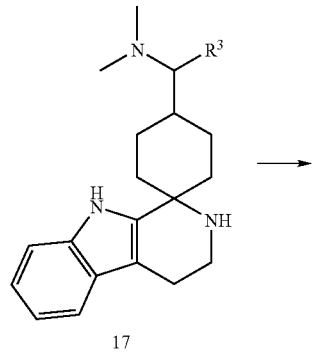

17

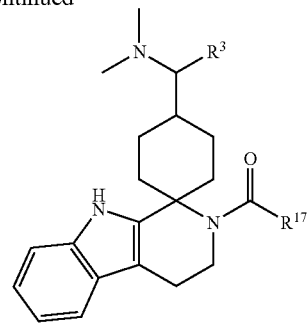

23, 24

Cyclohexyl{1,1-[3-(dimethylamino-(4-fluorophenyl)-methyl)-pentamethylene]-3,4-dihydro-1H-2,9-diazafluoren-2-yl}methanone ($R^3$=4-fluorophenyl, $R^{17}$=cyclohexyl) 23

1,1-[3-(Dimethylamino-(4-fluorophenyl)methyl)-pentamethylene]-3,4-dihydro-1H-2,9-diazafluorene 17 (75 mg, 0.19 mmol), dissolved in acetonitrile (2 ml), was initially introduced into a microwave glass and irradiated in a microwave oven with cyclohexanecarboxylic acid chloride (35 mg, 0.24 mmol), N-ethyl-diisopropylamine (31 mg, 0.24 mmol) and with DMAP (2 mg, 0.02 mmol) for 10 min at 120° C. The resulting suspension was quenched with saturated sodium bicarbonate solution and extracted with ethyl acetate. The aqueous phase was extracted twice more with MC. The combined organic phases were dried over magnesium sulfate, filtered with suction and concentrated. Purification was carried out by flash chromatography with ethyl acetate/hexane (2:1 with 5% triethylamine).

Yield: 73%
1H NMR (600 MHz, DMSO-$d_6$) 0.88-1.18 (m, 5 H) 1.19-1.34 (m, 2 H) 1.35-1.45 (m, 2 H) 1.46-1.55 (m, 1 H) 1.55-1.78 (m, 5 H) 1.77-1.90 (m, 1 H) 2.07 (s, 7 H) 2.55-2.68 (m, 3 H) 2.70-2.84 (m, 1 H) 2.87-3.06 (m, 2 H) 3.64-3.89 (m, 2 H) 6.92-6.93 (m, 1 H) 6.96-7.05 (m, 1 H) 7.08-7.17 (m, 2 H) 7.17-7.24 (m, 2 H) 7.24-7.33 (m, 2 H) 10.69 (s, 1 H)

Phenyl{1,1-[3-(dimethylamino-(4-fluorophenyl)-methyl)-pentamethylene]-3,4-di-hydro-1H-2,9-diazafluoren-2-yl}methanone ($R^3$=4-fluorophenyl, $R^{17}$=phenyl) 24

1,1-[3-(Dimethylamino-(4-fluorophenyl)methyl)-pentamethylene]-3,4-dihydro-1H-2,9-diazafluorene 17 (75 mg, 0.19 mmol), dissolved in acetonitrile (2 ml), was initially introduced into a microwave glass and irradiated in a microwave oven with benzoyl chloride (33 mg, 0.24 mmol), N-ethyl-diisopropylamine (31 mg, 0.24 mmol) and with DMAP (2 mg, 0.02 mmol) for 10 min at 120° C. The resulting suspension was quenched with saturated sodium bicarbonate solution and extracted with ethyl acetate. The aqueous phase was extracted twice more with MC. The combined organic phases were dried over magnesium sulfate, filtered with suction and concentrated. Purification was effected by flash chromatography with ethyl acetate/hexane (2:1 with 5% triethylamine).

Yield: 98%
1H NMR (600 MHz, DMSO-$d_6$) 1.09-1.29 (m, 3 H) 1.45-1.57 (m, 1 H) 1.77-1.91 (m, 2 H) 1.91-2.00 (m, 1 H) 2.05-2.20

(m, 7 H) 2.78-3.03 (m, 3 H) 3.03-3.18 (m, 1 H) 3.44-3.66 (m, 2 H) 6.93 (t, J=7.18 Hz, 1 H) 7.03 (t, J=7.55 Hz, 1 H) 7.09-7.20 (m, 4 H) 7.26 (dd, J=7.93, 5.67 Hz, 2 H) 7.30 (dd, J=17.37, 8.31 Hz, 2 H) 7.39 (t, J=7.55 Hz, 3 H) 7.48 (t, J=7.55 Hz, 1 H) 10.80 (s, 1 H)

Synthesis of the 1,1-[3-(dimethylamino-(aryl)-methyl)-pentamethylene]-1,3,4,9-tetrahydro-pyrano[3,4-b]indole Derivatives

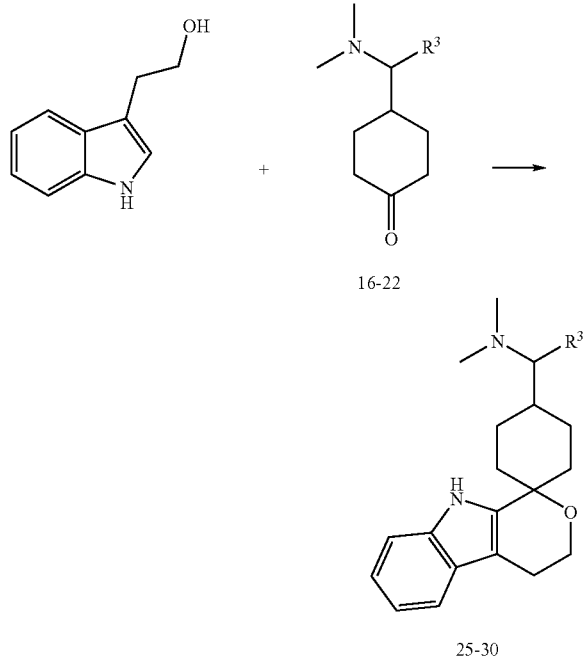

16-22

25-30

1,1-[3-(Dimethylamino-(4-fluorophenyl)-methyl)-pentamethylene]-1,3,4,9-tetrahydro-pyrano[3,4-b]indole ($R^3$=4-fluorophenyl) 25

The ketone 11 (250 mg, 1.0 mmol) and the tryptophol (161 mg, 1 mmol, Acros, order no. 14060) were dissolved in methylene chloride (5 ml) under argon and methanesulfonic acid (106 mg, 1.1 mmol) was added. The mixture was stirred at RT overnight, 1 N NaOH (10 ml) and $CH_2Cl_2$ (10 ml) were added, and the mixture was subsequently stirred for 30 min. After separation of the phases, the aqueous phase was extracted with $CH_2Cl_2$, and the organic phases were combined, dried ($Na_2SO_4$) and concentrated under reduced pressure. The residue was purified by flash chromatography with ethyl acetate/cyclohexane (2:1).

Yield: 113 mg (29%)

$^{13}$C-NMR ($CDCl_3$): 22.87; 24.75; 26.21; 36.02; 38.45; 41.08; 60.02; 72.62; 74.75; 107.44; 110.98; 114.65; 114.85; 118.36; 119.76; 121.83; 127.35; 130.70; 132.87; 135.78; 139.24; 160.77; 163.19.

1,1-[3-(Dimethylamino-(3-fluorophenyl)-methyl)-pentamethylene]-1,3,4,9-tetrahydro-pyrano[3,4-b]indole Citrate ($R^3$=3-fluorophenyl) 26

The ketone 12 (498 mg, 2 mmol) and the tryptophol (322 mg, 2 mmol, Acros, order no. 14060) were dissolved in methylene chloride (20 ml) under argon, and trifluoromethanesulfonic acid (0.18 ml, 2.028 mmol) was added. The mixture was stirred at RT overnight, the resulting precipitate was filtered out with suction and taken up in 2 N NaOH (5 ml) and methylene chloride (10 ml), and the mixture was subsequently stirred for 30 min. The phases were separated, the aqueous phase was extracted with $CH_2Cl_2$, and the organic phases were combined, dried ($Na_2SO_4$) and concentrated under reduced pressure.

Yield: 460 mg (58%), porous solid, 2 diastereomers $^{13}$C-NMR (DMSO-$d_6$): 20.95; 22.21; 22.40; 29.64; 29.75; 31.00; 34.07; 41.10; 43.12; 58.86; 65.03; 71.66; 71.88; 72.05; 73.29; 104.93; 110.74; 114.03; 114.23; 115.69; 115.85; 117.52; 117.79; 118.20; 120.37; 120.49; 125.53; 126.26; 129.61; 129.68; 135.22; 135.33; 137.29; 139.26; 139.66; 160.57; 162.99; 170.94; 174.85.

1,1-[3-(Dimethylamino-(phenyl)-methyl)-pentamethylene]-1,3,4,9-tetrahydropyrano[3,4-b]indole Citrate ($R^3$=phenyl) 27

The ketone 13 (462 mg, 2 mmol) and the tryptophol (322 mg, 2 mmol, Acros, order no. 14060) were dissolved in methylene chloride (100 ml) under argon and trifluoromethanesulfonic acid (0.18 ml, 2.03 mmol) was added. The mixture was stirred at RT for 6 hours, 2 N NaOH (5 ml) was added, and the mixture was subsequently stirred for 30 min. After separation of the phases, the aqueous phase was extracted with $CH_2Cl_2$, and the organic phases were combined, dried ($Na_2SO_4$) and concentrated under reduced pressure.

Yield: 740 mg (99%), porous solid, 2 diastereomers

The solid was dissolved in ethanol (5 ml) and citric acid (2 mmol) was added. In the refrigerator an oil settled out, the solution was decanted and ether was added to the residue. A colorless precipitate thereby precipitated and was filtered out with suction and dried.

Yield: 431 mg (38%), 2 diastereomers

Melting point: 162-165° C.

$^{13}$C-NMR ($CDCl_3$): 22.55; 22.93; 24.77; 25.59; 25.85; 34.68; 35.08; 37.89; 41.65; 42.72; 59.67; 59.82; 72.34; 72.58; 73.20; 75.05; 107.03; 110.65; 117.98; 118.09; 119.39; 121.46; 126.36; 126.72; 127.02; 127.16; 127.53; 127.78; 129.18; 129.43; 135.19; 135.44; 136.60; 137.57; 138.45; 139.03.

1,1-[3-(Dimethylamino-(phenylethyl)-methyl)-pentamethylene]-1,3,4,9-tetrahydropyrano[3,4-b]indole ($R^3$=phenethyl) 28

The ketone 14 (259 mg, 1.0 mmol) and tryptophol (161 mg, 1 mmol, Acros, order no. 14060) were dissolved in methylene chloride (5 ml) under argon and methanesulfonic acid (106 mg, 1.1 mmol) was added. The mixture was stirred at RT overnight, 1 N NaOH (10 ml) and $CH_2Cl_2$ (10 ml) were added and the mixture was subsequently stirred for 30 min. After separation of the phases, the aqueous phase was extracted with $CH_2Cl_2$, and the organic phases were combined, dried ($Na_2SO_4$) and concentrated under reduced pressure. The residue was purified by flash chromatography with ethyl acetate/cyclohexane (2:1).

Yield: 187 mg (46%), yellow oil $^{13}$C-NMR ($CDCl_3$): 22.59; 25.04; 26.42; 29.36; 35.36; 35.77; 35.84; 39.19; 41.23; 59.73; 68.08; 72.20; 107.00; 110.68; 118.07; 119.37; 121.45; 125.54; 127.01; 128.15; 128.22; 135.45; 138.98; 142.75.

1,1-[3-(Dimethylamino-(thiophen-2-yl)-methyl)-pentamethylene]-1,3,4,9-tetrahydro-pyrano[3,4-b]indole (R³=2-thiophene) 29

The ketone 15 (237 mg, 1 mmol) and the tryptophol (161 mg, 1 mmol, Acros, order no. 14060) were dissolved in methylene chloride (5 ml) under argon and methanesulfonic acid (106 mg, 1.1 mmol) was added. The mixture was stirred at RT overnight, 1 N NaOH (10 ml) and CH₂Cl₂ (10 ml) were added, and the mixture was subsequently stirred for 30 min. After separation of the phases, the aqueous phase was extracted with CH₂Cl₂, and the organic phases were combined, dried (Na₂SO₄) and concentrated under reduced pressure. The residue was purified by flash chromatography with ethyl acetate/cyclohexane (1:2).

Yield: 241 mg (63%), porous solid $^{13}$C-NMR (CDCl₃): 22.61; 23.60; 24.32; 33.37; 33.46; 36.41; 41.81; 59.82; 60.43; 65.77; 72.34; 72.84; 107.13; 110.72; 118.07; 119.40; 121.50; 123.88; 126.23; 126.42; 126.63; 135.37; 138.77; 140.10.

1,1-[3-(Dimethylamino-(4-chlorophenyl)-methyl)-pentamethylene]-1,3,4,9-tetrahydro-pyrano[3,4-b]indole (R³=4-chlorophenyl) 30

The ketone 16 (265 mg, 1 mmol) and the tryptophol (161 mg, 1 mmol, Acros, order no. 14060) were dissolved in methylene chloride (5 ml) under argon and methanesulfonic acid (106 mg, 1.1 mmol) was added. The mixture was stirred at RT overnight, 1 N NaOH (10 ml) and CH₂Cl₂ (10 ml) were added, and the mixture was subsequently stirred for 30 min. After separation of the phases, the aqueous phase was extracted with CH₂Cl₂, and the organic phases were combined, dried (Na₂SO₄) and concentrated under reduced pressure.

Yield: 404 mg (99%), porous solid $^{13}$C-NMR (CDCl₃): 22.54; 23.10; 24.38; 25.80; 33.95; 34.16; 34.70; 35.65; 37.95; 41.74; 42.23; 59.68; 59.80; 71.10; 72.29; 74.48; 107.06; 110.66; 118.10; 121.49; 121.62; 127.00; 127.75; 127.96; 130.33; 132.40; 135.32; 135.45; 138.87.

Synthesis of the 6-fluoro-1,1-[3-(dimethylamino-(aryl)-methyl)-pentamethylene]-1,3,4,9-tetrahydro-pyrano[3,4-b]indole Derivatives

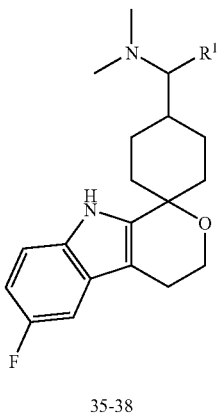

35-38

(5-Fluoro-3-hydroxy-2-oxo-2,3-dihydro-1H-indol-3-yl)acetic Acid Ethyl Ester 34

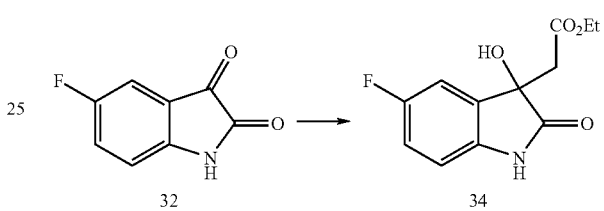

5-Fluoroisatin 32 (10 mmol, Lancaster, order no. 14553) was dissolved in a mixture of ethanol/pyridine/acetic acid (50 ml, 15:5:2), ethyl potassium malonate 33 (1.87 g, 11 mmol) was added, and the mixture was heated under reflux for 14 hours. The course of the reaction was monitored by TLC (eluent: ethyl acetate/hexane 1:1). The product was worked up by distilling off the solvent mixture under reduced pressure, taking up the residue in ethyl acetate (50 ml) and extracting the mixture by shaking with water (50 ml). After separation of the phases, the aqueous phase was extracted twice with 30 ml portions of ethyl acetate. The combined organic phases were washed with 2 N HCl (50 ml), dried over Na₂SO₄ and concentrated to 20 ml under reduced pressure. Hexane was added to the solution until the product started to crystallize. To bring the crystallization to completion, the mixture was cooled to 10° C. for 12 hours. The solid was filtered out with suction and dried in vacuo.

Yield: 89%

Melting point: 133-135° C.

2-(5-Fluoro-1H-indol-3-yl)ethanol 31

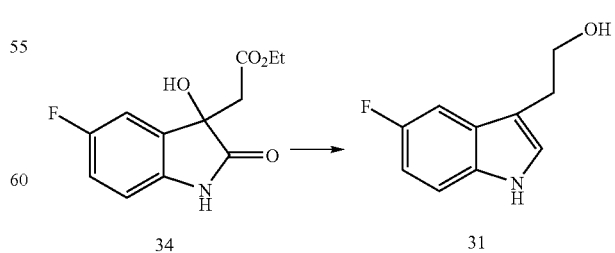

The aldol product 34 (10 mmol) was dissolved in absolute THF (20 ml) under an argon atmosphere. BH₃xTHF (40 ml, 1 M solution, 40 mmol) was then added to the mixture, and the mixture was stirred at room temperature for 14 hours. The course of the reaction was monitored of TLC. When the reaction had ended, the reaction solution was added to a mixture of ethyl acetate (50 ml) and H$_2$O (50 ml). After separation of the phases, the aqueous phase was extracted twice with 30 ml portions of ethyl acetate. The combined organic phases were dried over Na$_2$SO$_4$ and concentrated under reduced pressure. The residue was filtered over silica gel with ethyl acetate. After removal of the solvent, the product was obtained in the form of a sufficiently pure oil and crystallized spontaneously.

The $^1$H-NMR data corresponded to the literature: T. V. RajanBabu, B. L. Chendard, M. A. Petti, *J. Org. Chem.* 1986, 51, 1704-1712.

6-Fluoro-1,1-[3-(dimethylamino-(4-fluorophenyl)-methyl) -pentamethylene]-1,3,4,9-tetrahydropyrano[3,4-b]indole (R$^3$=4-fluorophenyl) 35

The ketone 11 (249 mg, 1.0 mmol) and the tryptophol derivative 31 (179 mg, 1.0 mmol) were dissolved in methylene chloride (5 ml) under argon, and methanesulfonic acid (106 mg, 1.1 mmol) was added. The mixture was stirred at RT overnight, 1 N NaOH (10 ml) and CH$_2$Cl$_2$ (10 ml) were added, and the mixture was subsequently stirred for 30 min. After separation of the phases, the aqueous phase was extracted with CH$_2$Cl$_2$, and the organic phases were combined, dried (Na$_2$SO$_4$) and concentrated under vacuo. The residue was purified by flash chromatography with ethyl acetate/cyclohexane (1:2).

Yield: 214 mg (52%), porous solid $^{13}$C-NMR (CDCl$_3$): 22.37; 22.97; 23.07; 25.04; 33.51; 34.11; 34.78; 42.02; 59.68; 71.13; 72.99; 103.10; 103.33; 107.62; 107.66; 109.66; 109.92; 111.19; 111.29; 114.63; 114.84; 127.00; 130.79; 131.88; 133.04; 140.67; 156.52; 159.05; 160.78; 163.22.

6-Fluoro-1,1-[3-(dimethylamino-(3-fluorophenyl)-methyl)-pentamethylene]-1,3,4,9-tetrahydropyrano[3,4-b]indole (R$^3$=3-fluorophenyl) 36

The ketone 12 (249 mg, 1.0 mmol) and the tryptophol derivative 31 (179 mg, 1 mmol) were dissolved in methylene chloride (5 ml) under argon, and methanesulfonic acid (106 mg, 1.1 mmol) was added. The mixture was stirred at RT overnight, 1 N NaOH (10 ml) and CH$_2$Cl$_2$ (10 ml) were added, and the mixture was subsequently stirred for 30 min. After separation of the phases, the aqueous phase was extracted with CH$_2$Cl$_2$, and the organic phases were combined, dried (Na$_2$SO$_4$) and concentrated under vacuo. The residue was purified by flash chromatography with ethyl acetate/cyclohexane (1:2).

Yield: 213 mg (52%), porous solid $^{13}$C-NMR (CDCl$_3$): 22.37; 23.10; 24.71; 33.68; 33.81; 34.48; 42.01; 59.68; 71.05; 72.91; 103.11; 103.34; 107.57; 107.61; 109.59; 109.86; 111.25; 111.35; 113.97; 114.19; 115.97; 116.17; 125.10; 127.04; 127.13; 129.26; 129.34; 131.90; 140.01; 140.07; 140.75; 156.72; 159.05; 161.47; 163.92.

6-Fluoro-1,1-[3-(dimethylamino-(phenyl)-methyl)-pentamethylene]-1,3,4,9-tetrahydro-pyrano[3,4-b]indole (R$^3$=phenyl) 37

The ketone 13 (231 mg, 1 mmol) and the tryptophol derivative 31 (179 mg, 1 mmol) were dissolved in methylene chloride (5 ml) under argon, and methanesulfonic acid (106 mg, 1.1 mmol) was added. The mixture was stirred at RT overnight, 1 N NaOH (10 ml) and CH$_2$Cl$_2$ (10 ml) were added, and the mixture was subsequently stirred for 30 min. After separation of the phases, the aqueous phase was extracted with CH$_2$Cl$_2$, and the organic phases were combined, dried (Na$_2$SO$_4$) and concentrated under vacuo. The residue was purified by flash chromatography with ethyl acetate/cyclohexane (1:2).

Yield: 215 mg (55%), porous solid $^{13}$C-NMR (CDCl$_3$): 22.40; 22.74; 23.07; 25.47; 34.31; 34.51; 34.95; 42.68; 59.69; 72.63; 73.15; 103.03; 103.25; 107.56; 107.61; 109.50; 109.76; 111.27; 111.36; 126.86; 126.96; 127.28; 127.92; 129.60; 131.82; 137.78; 140.59; 156.67; 159.00.

6-Fluoro-1,1-[3-(dimethylamino-(4-chlorophenyl)-methyl)-pentamethylene]-1,3,4,9-tetrahydropyrano[3,4-b]indole (R$^3$=4-chlorophenyl) 38

The ketone 16 (265 mg, 1.0 mmol) and the tryptophol derivative 31 (179 mg, 1.0 mmol) were dissolved in methylene chloride (5 ml) under argon, and methanesulfonic acid (106 mg, 1.1 mmol) was added. The mixture was stirred at RT overnight, 1 N NaOH (10 ml) and CH$_2$Cl$_2$ (10 ml) were added, and the mixture was subsequently stirred for 30 min. After separation of the phases, the aqueous phase was extracted with CH$_2$Cl$_2$, and the organic phases were combined, dried (Na$_2$SO$_4$) and concentrated under vacuo. The residue was purified by flash chromatography with ethyl acetate/cyclohexane (1:2).

Yield: 160 mg (37%), porous solid $^{13}$C-NMR (CDCl$_3$): 22.38; 22.91; 25.00; 26.91; 33.89; 34.10; 34.65; 42.02; 42.23; 59.69; 71.27; 72.97; 103.09; 103.32; 107.64; 107.69; 109.68; 109.95; 111.27; 111.37; 126.98; 127.08; 128.10; 130.75; 131.89; 132.98; 135.88; 140.60; 156.73; 159.06.

Synthesis of the 3,6-dimethyl-1,1-[3-(dimethylamino-(aryl)-methyl) -pentamethylene]-1,3,4,9-tetrahydropyrano[3,4-b]indole Derivatives

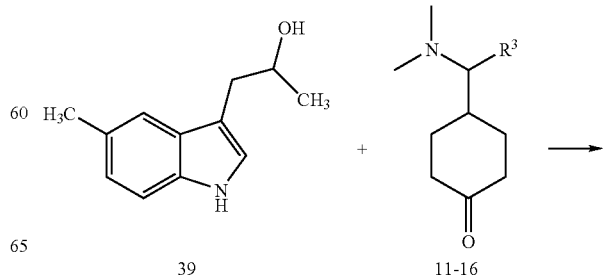

1-(5-Methyl-1H-indol-3-yl)propan-2-ol 39

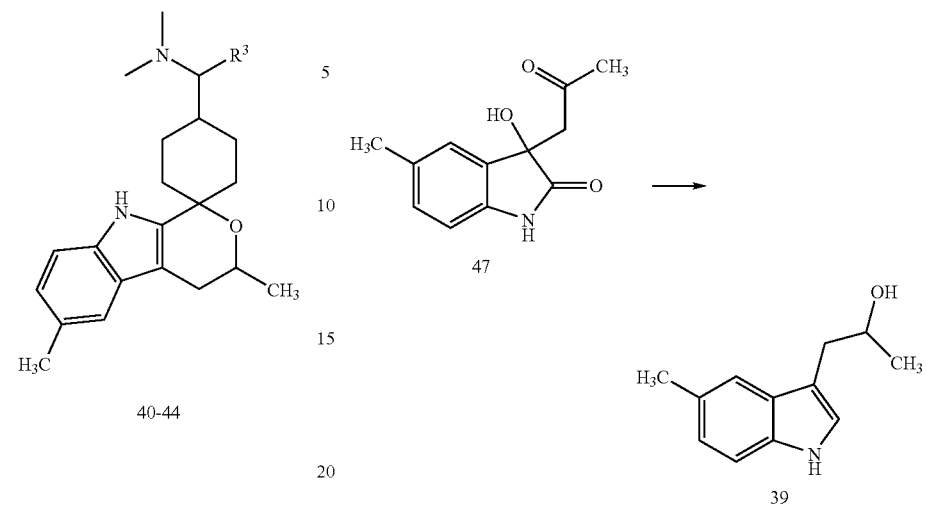

The synthesis of 1-(5-methyl-1H-indol-3-yl)propan-2-ol 39 was carried out analogously to the method of S. J. Garden, R. B. da Silva and A. C. Pinto in *Tetrahedron* 2002, 58, 8399-8412.

3-Hydroxy-5-methyl-3-(2-oxo-propyl)-1,3-dihydro-indol-2-one 47

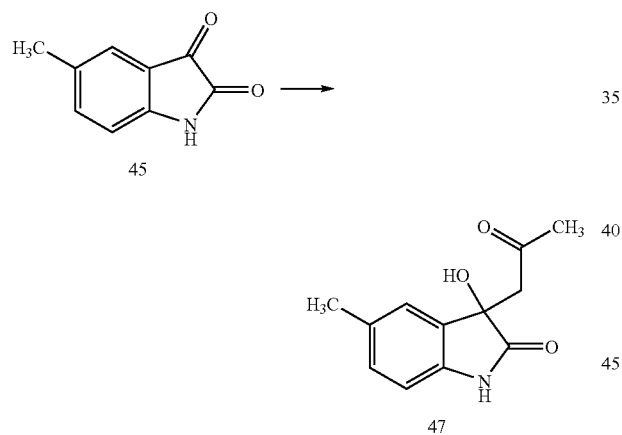

5-Methylisatin 45 (10 mmol, Lancaster, order no. 8009) was dissolved in acetone 46 (50 ml), $K_2CO_3$ (138 mg, 1 mmol) was added, and the mixture was stirred at room temperature for 24 hours. The course of the reaction was monitored by TLC (eluent: ethyl acetate). The reaction solution was worked up by concentrating to 40 ml in vacuo, during which the product started to precipitate. To complete the precipitation the solution was cooled to approx. 10° C. in a refrigerator overnight. The product which precipitated was filtered out with suction and dried in vacuo. It was possible to isolate further reaction product by removing the acetone completely and dissolving the residue which remained in ethyl acetate. The solid formed during subsequent precipitation with hexane was filtered out with suction and dried in vacuo.

Yield: 74%

Melting point: 158° C.

The aldol product 47 (10 mmol) was dissolved in absolute THF (20 ml) under an Ar atmosphere. $BH_3$xTHF (30 ml, 1 M solution, 30 mmol) was then added to the mixture, while cooling with a water bath, and the mixture was stirred at room temperature for 15 hours. The course of the reaction was monitored by TLC. When the reaction had ended, the reaction solution was added to a mixture of ethyl acetate (50 ml) and $H_2O$ (50 ml). After separation of the phases, the aqueous phase was extracted twice with 30 ml portions of ethyl acetate. The combined organic phases were dried over $Na_2SO_4$ and concentrated in vacuo. The residue was filtered over silica gel with ethyl acetate. The crude product obtained after removal of the solvent was purified by column chromatography on silica gel (eluent:ethyl acetate/cyclohexane: 1:2).

Yield: 78%

3,6-Dimethyl-1,1-[3-(dimethylamino-(4-fluorophenyl)-methyl)-pentamethylene]-1,3,4,9-tetrahydropyrano[3,4-b]indole ($R^3$=4-fluorophenyl) 40

The ketone 11 (249 mg, 1.0 mmol) and the tryptophol derivative 39 (189 mg, 1 mmol) were dissolved in methylene chloride (5 ml) under argon and methanesulfonic acid (106 mg, 1.1 mmol) was added. The mixture was stirred at RT overnight, 1 N NaOH (10 ml) and $CH_2Cl_2$ (10 ml) were added, and the mixture was subsequently stirred for 30 min. After separation of the phases, the aqueous phase was extracted with $CH_2Cl_2$, and the organic phases were combined, dried ($Na_2SO_4$) and concentrated under vacuo. The residue was purified by flash chromatography with ethyl acetate/cyclohexane (2:1).

Yield: 209 mg (50%), porous solid $^{13}$C-NMR (CDCl$_3$): 22.13; 22.35; 23.50; 24.87; 25.77; 26.00; 26.21; 26.75; 27.34; 30.30; 30.61; 33.68; 34.28; 35.42; 36.08; 38.29; 38.45; 42.04; 42.07; 42.52; 42.62; 65.65; 65.75; 72.92; 74.68; 77.44; 107.61; 110.62; 114.55; 114.58; 114.78; 115.07; 118.06; 118.17; 123.12; 123.30; 127.49; 128.88; 130.73; 130.81; 130.97; 131.04; 132.80; 132.86; 132.89; 134.14; 134.30; 139.65; 160.75; 163.17.

3,6-Dimethyl-1,1-[3-(dimethylamino-(3-fluorophenyl)-methyl)-pentamethylene]-1,3,4,9-tetrahydropyrano[3,4-b]indole ($R^3$=3-fluorophenyl) 41

The ketone 12 (249 mg, 1 mmol) and the tryptophol derivative 39 (189 mg, 1 mmol) were dissolved in methylene chloride (5 ml) under argon and methanesulfonic acid (106 mg, 1.1 mmol) was added. The mixture was stirred at RT overnight, 1 N NaOH (10 ml) and CH$_2$Cl$_2$ (10 ml) were added, and the mixture was subsequently stirred for 30 min. After separation of the phases, the aqueous phase was extracted with CH$_2$Cl$_2$, and the organic phases were combined, dried (Na$_2$SO$_4$) and concentrated under vacuo. The residue was purified by flash chromatography with ethyl acetate/cyclohexane (1:2).

Yield: 277 mg (65%), porous solid $^{13}$C-NMR (CDCl$_3$): 21.55; 21.80; 22.02; 23.35; 25.25; 30.05; 33.21; 33.87; 34.90; 35.49; 38.01; 41.71; 42.10; 42.18; 65.43; 71.24; 72.57; 73.33; 74.70; 107.32; 110.32; 113.84; 114.04; 115.87; 116.07; 117.76; 122.81; 122.93; 125.00; 126.69; 128.60; 129.07; 129.16; 133.87; 138.97; 140.04; 140.09; 161.27; 163.70.

3,6-Dimethyl-1,1-[3-(dimethylamino-(phenyl)-methyl)-pentamethylene]-1,3,4,9-tetrahydropyrano[3,4-b]indole Citrate (R$^3$=phenyl) 42

The ketone 13 (231 mg, 1 mmol) and the tryptophol derivative 39 (189 mg, 1 mmol) were dissolved in methylene chloride (10 ml) under argon, and trifluoromethanesulfonic acid (0.09 ml, 1.014 mmol) was added. The mixture was stirred at RT overnight, 2 N NaOH (2 ml) was added, and the mixture was subsequently stirred for 30 min. After separation of the phases, the aqueous phase was extracted with CH$_2$Cl$_2$, and the organic phases were combined, dried (Na$_2$SO$_4$) and concentrated under vacuo. The oil which remained was dissolved in ethanol (3 ml), and citric acid (1.2 mmol) was added. Since no solid crystallized out, the solution was concentrated, the residue was boiled up with acetonitrile (20 ml), and the crystals formed were filtered out with suction.

Yield: 160 mg (27%), 2 diastereomers

Melting point: 245-250° C.

$^{13}$C-NMR (DMSO-d$_6$): 20.77; 21.22; 21.77; 22.22; 22.63; 27.88; 29.66; 31.01; 31.98; 32.22; 36.69; 40.94; 43.55; 64.65; 65.49; 71.66; 72.34; 104.72; 110.39; 117.13; 121.80; 126.36; 126.46; 127.24; 127.75; 129.29; 133.85; 139.89; 170.90; 175.48.

3,6-Dimethyl-1,1-[3-(dimethylamino-(phenylethyl)-methyl)-pentamethylene]-1,3,4,9-tetrahydropyrano[3,4-b]indole (R$^3$=phenethyl) 43

The ketone 14 (259 mg, 1.0 mmol) and the tryptophol derivative 39 (189 mg, 1 mmol) were dissolved in methylene chloride (5 ml) under argon, and methanesulfonic acid (106 mg, 1.1 mmol) was added. The mixture was stirred at RT overnight, 1 N NaOH (10 ml) and CH$_2$Cl$_2$ (10 ml) were added, and the mixture was subsequently stirred for 30 min. After separation of the phases, the aqueous phase was extracted with CH$_2$Cl$_2$, and the organic phases were combined, dried (Na$_2$SO$_4$) and concentrated under vacuo. The product was purified by flash chromatography with ethyl acetate/cyclohexane (2:1).

Yield: 159 mg (37%), porous solid $^{13}$C-NMR (CDCl$_3$): 21.93; 24.95; 26.41; 29.42; 30.06; 34.13; 35.38; 35.58; 38.09; 39.29; 41.21; 65.42; 68.11; 68.26; 72.51; 107.13; 110.32; 117.84; 122.81; 125.56; 127.22; 128.18; 128.21; 128.56; 134.03; 139.40; 142.85; 142.89.

3,6-Dimethyl-1,1-[3-(dimethylamino-(4-chlorophenyl)-methyl)-pentamethylene]-1,3,4,9-tetrahydropyrano[3,4-b]indole (R$^3$=4-chlorophenyl) 44

The ketone 16 (265 mg, 1 mmol) and the tryptophol derivative 39 (189 mg, 1 mmol) were dissolved in methylene chloride (5 ml) under argon, and methanesulfonic acid (106 mg, 1.1 mmol) was added. The mixture was stirred at RT overnight, 1 N NaOH (10 ml) and CH$_2$Cl$_2$ (10 ml) were added, and the mixture was subsequently stirred for 30 min. After separation of the phases, the aqueous phase was extracted with CH$_2$Cl$_2$, and the organic phases were combined, dried (Na$_2$SO$_4$) and concentrated under vacuo. The residue was purified by flash chromatography with ethyl acetate/cyclohexane (1:2).

Yield: 300 mg (68%), porous solid $^{13}$C-NMR (CDCl$_3$): 21.55; 22.01; 23.39; 24.59; 25.43; 25.82; 27.03; 29.99; 30.04; 30.29; 33.39; 33.86; 33.95; 34.84; 35.00; 35.80; 37.76; 37.98; 41.65; 41.71; 42.22; 42.33; 65.36; 65.43; 71.25; 72.57; 73.39; 74.43; 107.14; 107.33; 110.29; 117.72; 122.81; 123.01; 126.61; 127.20; 127.69; 128.56; 130.37; 132.40; 132.80; 133.86; 134.02; 135.27; 135.38; 135.81; 138.82; 139.29.

Synthesis of the 6-fluoro-3-methyl-1,1-[3-(dimethylamino-(aryl)-methyl)-pentamethylene]-1,3,4,9-tetrahydropyrano[3,4-b]indole Derivatives

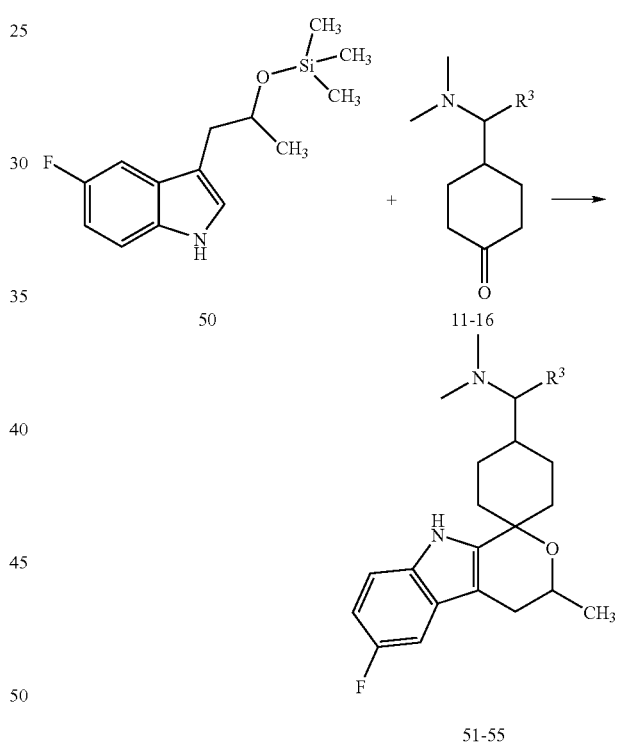

5-Fluoro-3-hydroxy-3-(2-oxo-propyl)-1,3-dihydroindol-2-one 48

5-Fluoroisatin 32 (10 mmol, Lancaster, order no. 14553) was dissolved in acetone 46 (50 ml), K$_2$CO$_3$ (138 mg, 1 mmol) was added, and the mixture was stirred at room temperature for 5 hours. The course of the reaction was monitored by TLC (eluent: ethyl acetate). To work up the product the acetone was completely distilled off in vacuo. The residue was dissolved in ethyl acetate, and the solution was filtered over silica gel with ethyl acetate. The filtrate was concentrated to 20 ml, and hexane was added until precipitation started. To complete the precipitation, the solution was cooled to approx. 10° C. in a refrigerator overnight. The product which precipitated was filtered out with suction and dried in vacuo. The resulting crude product was recrystallized from ethyl acetate/hexane (1:4).

Yield: 90%
Melting point: 153-155° C.

The $^1$H-NMR data corresponded to the literature: G. K. Jnaneshwara, V. H. Deshpande, *Synthetic Commun.* 1999, 29, 20, 3627-3633.

1-(5-Fluoro-1H-indol-3-yl)propan-2-ol 49

The aldol product 48 (10 mmol) was dissolved in absolute THF (20 ml) under an Ar atmosphere. BH$_3$xTHF (30 ml, 1 M solution, 30 mmol) was then added to the mixture, while cooling with a water bath, and the mixture was stirred at room temperature for 4 h. The course of the reaction was monitored by TLC. When the reaction had ended, the reaction solution was added to a mixture of ethyl acetate (50 ml) and H$_2$O (50 ml). After separation of the phases, the aqueous phase was extracted twice with ethyl acetate (30 ml each time). The combined organic phases were dried over Na$_2$SO$_4$ and concentrated under vacuo. The residue was filtered over silica gel with ethyl acetate. After removal of the solvent, the product was obtained in the form of a sufficiently pure oil and crystallizes spontaneously.

Yield: 92%
Melting point: 74-76° C.

For the subsequent synthesis of the spiro compounds, it may be necessary to activate the 3-(2-hydroxypropyl)-1H-indoles obtained for subsequent synthesis of the spiro compounds. This is effected by silylation of the alcohol function.

5-Fluoro-3-(2-trimethylsilanyloxy-propyl)-1H-indole 50

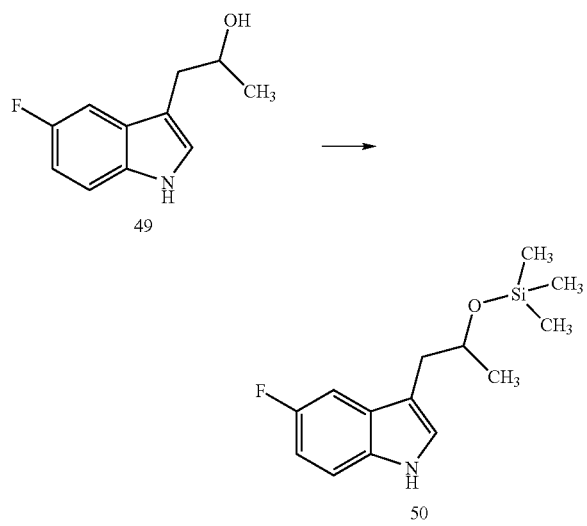

The alcohol 49 (10 mmol) was dissolved in absolute THF (15 ml) with exclusion of moisture. Trimethylchlorosilane (2.1 ml, 15.3 mmol) and hexamethyldisilazane (4.9 ml, 23.3 mmol) were added, and the mixture was stirred at room temperature for 24 hours. The course of the reaction was monitored by thin layer chromatography. When the reaction had ended, the solvent was removed under vacuo. The remaining residue was a viscous oil which was taken up in diethyl ether (30 ml), and saturated NaHCO$_3$ (30 ml) was added. The phases were separated, and the aqueous phase was extracted twice with 15 ml portions of Et$_2$O. The combined organic phases were dried over Na$_2$SO$_4$ and concentrated under vacuo. The resulting product was initially in the form of an oil and crystallized spontaneously. The crude product was further purified by recrystallization from hexane.

Yield: 88%
Melting point: 56-58° C.

6-Fluoro-3-methyl-1,1-[3-(dimethylamino-(4-fluorophenyl)-methyl)-pentamethylene]-1,3,4,9-tetrahydropyrano[3,4-b]indole (R$^3$=4-fluorophenyl) 51

The ketone 11 (249 mg, 1.0 mmol) and the tryptophol derivative 50 (265 mg, 1 mmol) were dissolved in methylene chloride (5 ml) under argon, and methanesulfonic acid (106 mg, 1.1 mmol) was added. The mixture was stirred at RT overnight, 1 N NaOH (10 ml) and CH$_2$Cl$_2$ (10 ml) were added, and the mixture was subsequently stirred for 30 min. After separation of the phases, the aqueous phase was extracted with CH$_2$Cl$_2$, and the organic phases were combined, dried (Na$_2$SO$_4$) and concentrated under vacuo. The product was purified by flash chromatography with ethyl acetate/cyclohexane (2:1).

Yield: 348 mg (82%), porous solid
$^{13}$C-NMR (CDCl$_3$): 21.74; 21.94; 24.31; 24.52; 25.61; 25.83; 27.01; 29.85; 30.28; 33.36; 33.83; 37.70; 37.91; 38.09; 41.68; 41.71; 42.33; 65.27; 72.57; 74.34; 103.06; 103.29; 107.84; 107.87; 109.20; 109.46; 111.07; 111.16; 114.23; 114.43; 127.30; 127.40; 130.39; 130.46; 130.65; 132.17; 132.50; 141.21; 156.50; 158.82; 160.42; 162.85.

6-Fluoro-3-methyl-1,1-[3-(dimethylamino-(3-fluorophenyl)-methyl)-pentamethylene]-1,3,4,9-tetrahydropyrano[3,4-b]indole (R$^3$=3-fluorophenyl) 52

The ketone 12 (249 mg, 1 mmol) and the tryptophol derivative 50 (265 mg, 1 mmol) were dissolved in methylene chloride (5 ml) under argon, and methanesulfonic acid (106 mg, 1.1 mmol) was added. The mixture was stirred at RT overnight, 1 N NaOH (10 ml) and CH$_2$Cl$_2$ (10 ml) were added, and the mixture was subsequently stirred for 30 min. After separation of the phases, the aqueous phase was extracted with CH$_2$Cl$_2$, and the organic phases were combined, dried (Na$_2$SO$_4$) and concentrated under vacuo. The residue was purified by flash chromatography with ethyl acetate/cyclohexane (1:2).

Yield: 80 mg (19%), porous solid
$^{13}$C-NMR (CDCl$_3$): 21.74; 21.94; 24.31; 24.52; 25.61; 25.83; 27.01; 29.85; 30.28; 33.36; 33.83; 37.70; 37.91; 38.09; 41.68; 41.71; 42.33; 65.27; 72.57; 74.34; 103.06; 103.29; 107.84; 107.87; 109.20; 109.46; 111.07; 111.16; 114.23; 114.43; 127.30; 127.40; 130.39; 130.46; 130.65; 132.17; 132.50; 141.21; 156.50; 158.82; 160.42; 162.85.

6-Fluoro-3-methyl-1,1-[3-(dimethylamino-(phenyl)-methyl)-pentamethylene]-1,3,4,9-tetrahydropyrano[3,4-b]indole (R$^3$=phenyl) 53

The ketone 13 (231 mg, 1 mmol) and the tryptophol derivative 50 (265 mg, 1 mmol) were dissolved in methylene chloride (5 ml) under argon, and methanesulfonic acid (106 mg, 1.1 mmol) was added. The mixture was stirred at RT overnight, 1 N NaOH (10 ml) and CH$_2$Cl$_2$ (10 ml) were added, and the mixture was subsequently stirred for 30 min. After separation of the phases, the aqueous phase was extracted with CH$_2$Cl$_2$, and the organic phases were combined, dried (Na$_2$SO$_4$) and concentrated under vacuo. The residue was purified by flash chromatography with ethyl acetate/cyclohexane (1:2).

Yield: 128 mg (31%), porous solid $^{13}$C-NMR (CDCl$_3$): 21.74; 21.96; 22.81; 24.61; 25.61; 25.94; 27.01; 29.87; 30.29; 33.99; 35.30; 35.90; 37.77; 37.90; 41.65; 42.75; 42.87; 65.27; 65.36; 72.60; 72.97; 75.02; 75.28; 102.89; 103.31; 107.84; 108.00; 109.28; 109.54; 111.06; 111.26; 126.74; 127.33; 127.49; 127.78; 129.20; 129.49; 131.92; 132.15; 136.56; 137.79; 140.61; 141.31; 156.50; 158.83.

6-Fluoro-3-methyl-1,1-[3-(dimethylamino-(phenylethyl)-methyl)-pentamethylene]-1,3,4,9-tetrahydropyrano[3,4-b]indole (R$^3$=phenethyl) 54

The ketone 14 (259 mg, 1.0 mmol) and the tryptophol derivative 50 (265 mg, 1 mmol) were dissolved in methylene chloride (5 ml) under argon and methanesulfonic acid (106 mg, 1.1 mmol) was added. The mixture was stirred at RT overnight, 1 N NaOH (10 ml) and CH$_2$Cl$_2$ (10 ml) were added, and the mixture was subsequently stirred for 30 min. After separation of the phases, the aqueous phase was extracted with CH$_2$Cl$_2$, and the organic phases were combined, dried (Na$_2$SO$_4$) and concentrated under vacuo. The residue was purified by flash chromatography with ethyl acetate/cyclohexane (2:1).

Yield: 149 mg (34%), porous solid $^{13}$C-NMR (CDCl$_3$): 21.74; 21.94; 24.31; 24.52; 25.61; 25.83; 27.01; 29.85; 30.28; 33.36; 33.83; 37.70; 37.91; 38.09; 41.68; 41.71; 42.33; 65.27; 72.57; 74.34; 103.06; 103.29; 107.84; 107.87; 109.20; 109.46; 111.07; 111.16; 114.23; 114.43; 127.30; 127.40; 130.39; 130.46; 130.65; 132.17; 132.50; 141.21; 156.50; 158.82; 160.42; 162.85.

6-Fluoro-3-methyl-1,1-[3-(dimethylamino-(4-chlorophenyl)-methyl)-penta-methylene]-1,3,4,9-tetrahydropyrano[3,4-b]indole (R$^3$=4-chlorophenyl) 55

The ketone 16 (265 mg, 1 mmol) and the tryptophol derivative 50 (265 mg, 1 mmol) were dissolved in methylene chloride (5 ml) under argon, and methanesulfonic acid (106 mg, 1.1 mmol) was added. The mixture was stirred at RT overnight, 1 N NaOH (10 ml) and CH$_2$Cl$_2$ (10 ml) were added, and the mixture was subsequently stirred for 30 min. After separation of the phases, the aqueous phase was extracted with CH$_2$Cl$_2$, and the organic phases were combined, dried (Na$_2$SO$_4$) and concentrated under vacuo. The residue was purified by flash chromatography with ethyl acetate/cyclohexane (1:2).

Yield: 93 mg (21%), porous solid $^{13}$C-NMR (CDCl$_3$): 21.61; 24.27; 25.41; 25.61; 26.88; 29.72; 30.15; 33.81; 37.58; 37.78; 41.52; 42.34; 43.44; 65.28; 75.52; 74.34; 103.17; 103.40; 107.95; 108.00; 109.35; 109.61; 111.14; 111.24; 127.39; 127.49; 127.84; 128.08; 130.49; 130.75; 132.23; 132.56; 135.23; 141.26; 156.69; 159.01.

Automated Synthesis 1 ml of a solution of the corresponding 1,1-[3-(dimethylamino-phenylmethyl)-pentamethylene]-3,4-dihydro-1H-2,9-diazafluorene derivative (0.1 M in MC, 100 µmol) was initially introduced into a microwave glass and 1 ml of the corresponding acid chloride solution (0.2 M in MC, 200 µmol) and 0.5 ml of N-ethyldiisopropylamine solution (0.4 M, 200 µmol) were added. The microwave reaction glass was then sealed and irradiated in a microwave oven (Biotage) at 120° C. for 10 min (prestirring for 10 s, absorption level normal). After the reaction had taken place, the reaction solution was transferred into a tared vessel and concentrated to dryness in a GeneVac. Purification was carried out by means of RP-HPLC. The following compounds were synthesized by this method. Analysis was carried out by mass spectrometry.

| No. | Name | m/z |
| --- | --- | --- |
| 56 | 1-{1,1-[3-(dimethylamino-phenylmethyl)-pentamethylene]-3,4-dihydro-1H-2,9-diazafluoren-2-yl}-3,3-dimethylbutan-1-one | 472.4 [M$^+$ + 1] |
| 57 | 2-[(3,4-dimethoxyphenyl)acetyl]-{1,1-[3-(dimethylamino-phenylmethyl)-pentamethylene]-3,4-dihydro-1H-2,9-diazafluorene} | 552.4 [M$^+$ + 1] |
| 58 | 1-{1,1-[3-(dimethylamino-phenylmethyl)-pentamethylene]-3,4-dihydro-1H-2,9-diazafluoren-2-yl}-2-methyl-3-phenylprop-2-en-1-one | 329.4 [M$^+$ + 1] |
| 59 | 2-(cyclohexylcarbonyl)-{1,1-[3-(dimethylamino-phenylmethyl)-pentamethylene]-3,4-dihydro-1H-2,9-diazafluorene} | 518.4 [M$^+$ + 1] |
| 60 | 2-[(4-chlorophenoxy)acetyl]-{1,1-[3-(dimethylamino-phenylmethyl)-pentamethylene]-3,4-dihydro-1H-2,9-diazafluorene} | 542.4; 544.4 [M$^+$ + 1] |
| 61 | 1-{1,1-[3-(dimethylamino-phenylmethyl)-pentamethylene]-3,4-dihydro-1H-2,9-diazafluoren-2-yl}-3-(2-chlorophenyl)prop-2-en-1-one | 531.3; 533.3 [M$^+$ + 1], 266.4, 268.4 |
| 62 | 1-{1,1-[3-(dimethylamino-(4-fluorophenyl)methyl)-pentamethylene]-3,4-dihydro-1H-2,9-diazafluoren-2-yl}-3,3-dimethylbutan-1-one | 490.4 [M$^+$ + 1] |
| 63 | 2-[(3,4-dimethoxyphenyl)acetyl]-{1,1-[3-(dimethylamino-(4-fluorophenyl)methyl)-pentamethylene]-3,4-dihydro-1H-2,9-diazafluorene} | 570.4 [M$^+$ + 1] |
| 64 | 1-{1,1-[3-(dimethylamino-(4-fluorophenyl)methyl)-pentamethylene]-3,4-dihydro-1H-2,9-diazafluoren-2-yl}-2-methyl-3-phenylprop-2-en-1-one | 536.4 [M$^+$ + 1] |
| 65 | 2-[(4-chlorophenoxy)acetyl]-{1,1-[3-(dimethylamino-(4-fluorophenyl)methyl)-pentamethylene]-3,4-dihydro-1H-2,9-diazafluorene} | 560.3; 562.3 [M$^+$ + 1] |
| 66 | 1-{1,1-[3-(dimethylamino-(3-fluorophenyl)methyl)-pentamethylene]-3,4-dihydro-1H-2,9-diazafluoren-2-yl}-3,3-dimethylbutan-1-one | 490.4 [M$^+$ + 1] |
| 67 | 2-[(3,4-dimethoxyphenyl)acetyl]-{1,1-[3-(dimethylamino-(3-fluorophenyl)methyl)-pentamethylene]-3,4-dihydro-1H-2,9-diazafluorene} | 570.4 [M$^+$ + 1] |
| 68 | 1-{1,1-[3-(dimethylamino-(3-fluorophenyl)methyl)-pentamethylene]-3,4-dihydro-1H-2,9-diazafluoren-2-yl}-2-methyl-3-phenylprop-2-en-1-one | 536.4 [M$^+$ + 1] |
| 69 | 2-(cyclohexylcarbonyl)-{1,1-[3-(dimethylamino-(3-fluorophenyl)methyl)-pentamethylene]-3,4-dihydro-1H-2,9-diazafluorene} | 502.4 [M$^+$ + 1] |
| 70 | 2-[(4-chlorophenoxy)acetyl]-{1,1-[3-(dimethylamino-(3-fluorophenyl)methyl)-pentamethylene]-3,4-dihydro-1H-2,9-diazafluorene} | 560.3; 562.3 [M$^+$ + 1] |
| 71 | 2-(1-benzothien-2-ylcarbonyl)-{1,1-[3-(dimethylamino-(3-fluorophenyl)methyl)-pentamethylene]-3,4-dihydro-1H-2,9-diazafluorene} | 552.3 [M$^+$ + 1] |

-continued

| No. | Name | m/z |
|---|---|---|
| 72 | 1-{1,1-[3-(dimethylamino-(3-fluorophenyl)methyl)-pentamethylene]-3,4-dihydro-1H-2,9-diazafluoren-2-yl}-3-(2-chlorophenyl)prop-2-en-1-one | 556.3, 558.3 [M⁺ + 1] |
| 73 | 1-{1,1-[3-(dimethylamino-(4-chlorophenyl)methyl)-pentamethylene]-3,4-dihydro-1H-2,9-diazafluoren-2-yl}-3,3-dimethylbutan-1-one | 506.4, 508.3 [M⁺ + 1] |
| 74 | 2-[(3,4-dimethoxyphenyl)acetyl]-{1,1-[3-(dimethylamino-(4-chlorophenyl)methyl)-pentamethylene]-3,4-dihydro-1H-2,9-diazafluorene} | [586.4, 588.3 M⁺ + 1] |
| 75 | 1-{1,1-[3-(dimethylamino-(4-chlorophenyl)methyl)-pentamethylene]-3,4-dihydro-1H-2,9-diazafluoren-2-yl}-2-methyl-3-phenylprop-2-en-1-one | 552.4, 554.2 [M⁺ + 1] |
| 76 | 2-(cyclohexylcarbonyl)-{1,1-[3-(dimethylamino-(4-chlorophenyl)methyl)-pentamethylene]-3,4-dihydro-1H-2,9-diazafluorene} | 518.4, 520.4 [M⁺ + 1] |
| 77 | 2-[(4-chlorophenoxy)acetyl]-{1,1-[3-(dimethylamino-(4-chlorophenyl)-methyl)-pentamethylene]-3,4-dihydro-1H-2,9-diazafluorene} | 576.3, 578.3 [M⁺ + 1] |
| 78 | 2-(1-benzothien-2-ylcarbonyl)-{1,1-[3-(dimethylamino-(4-chlorophenyl)-methyl)-pentamethylene]-3,4-dihydro-1H-2,9-diazafluorene} | 568.3, 570.3 [M⁺ + 1] |
| 79 | 2-acetyl-{1,1-[3-(dimethylamino-phenylmethyl)-pentamethylene]-3,4-dihydro-1H-2,9-diazafluorene} | 416.3 [M⁺ + 1] |
| 80 | 1-{1,1-[3-(dimethylamino-phenylmethyl)-pentamethylene]-3,4-dihydro-1H-2,9-diazafluoren-2-yl}-3-phenylprop-2-en-1-one | 504.3 [M⁺ + 1] |
| 81 | 2-(methoxyacetyl)-{1,1-[3-(dimethylamino-phenylmethyl)-pentamethylene]-3,4-dihydro-1H-2,9-diazafluorene} | 446.3 [M⁺ + 1] |
| 82 | 2-(2-thienylacetyl)-{1,1-[3-(dimethylamino-phenylmethyl)-pentamethylene]-3,4-dihydro-1H-2,9-diazafluorene} | 498.3 [M⁺ + 1] |
| 83 | 2-(benzyloxyacetyl)-{1,1-[3-(dimethylamino-phenylmethyl)-pentamethylene]-3,4-dihydro-1H-2,9-diazafluorene} | 522.3 [M⁺ + 1] |
| 84 | acetyl-{1,1-[3-(dimethylamino-(4-fluorophenyl)methyl)-pentamethylene]-3,4-dihydro-1H-2,9-diazafluorene} | 434.3 [M⁺ + 1] |
| 85 | 2-(3-cyclopentylpropanoyl)-{1,1-[3-(dimethylamino-(4-fluorophenyl)-methyl)-pentamethylene]-3,4-dihydro-1H-2,9-diazafluorene} | 516.4 [M⁺ + 1] |
| 86 | 1-{1,1-[3-(dimethylamino-(4-fluorophenyl)methyl)-pentamethylene]-3,4-dihydro-1H-2,9-diazafluoren-2-yl}-3-phenylprop-2-en-1-one | 522.4 [M⁺ + 1] |
| 87 | 2-(2-thienylacetyl)-{1,1-[3-(dimethylamino-(4-fluorophenyl)methyl)-pentamethylene]-3,4-dihydro-1H-2,9-diazafluorene} | 516.4 [M⁺ + 1] |
| 88 | 2-(benzyloxyacetyl)-{1,1-[3-(dimethylamino-(4-fluorophenyl)methyl)-pentamethylene]-3,4-dihydro-1H-2,9-diazafluorene} | 540.3 [M⁺ + 1] |
| 89 | acetyl-{1,1-[3-(dimethylamino-(3-fluorophenyl)methyl)-pentamethylene]-3,4-dihydro-1H-2,9-diazafluorene} | 434.3 [M⁺ + 1] |
| 90 | 2-(3-cyclopentylpropanoyl)-{1,1-[3-(dimethylamino-(3-fluorophenyl)-methyl)-pentamethylene]-3,4-dihydro-1H-2,9-diazafluorene} | 516.3 [M⁺ + 1] |
| 91 | 2-(cyclopropylcarbonyl)-{1,1-[3-(dimethylamino-(3-fluorophenyl)methyl)-pentamethylene]-3,4-dihydro-1H-2,9-diazafluorene} | 460.3 [M⁺ + 1] |
| 92 | 2-(methoxyacetyl)-{1,1-[3-(dimethylamino-(3-fluorophenyl)methyl)-pentamethylene]-3,4-dihydro-1H-2,9-diazafluorene} | 464.3 [M⁺ + 1] |
| 93 | 2-(2-thienylacetyl)-{1,1-[3-(dimethylamino-(3-fluorophenyl)methyl)-pentamethylene]-3,4-dihydro-1H-2,9-diazafluorene} | 516.3 [M⁺ + 1] |
| 94 | 2-(benzyloxyacetyl)-{1,1-[3-(dimethylamino-(3-fluorophenyl)methyl)-pentamethylene]-3,4-dihydro-1H-2,9-diazafluorene} | 540.3 [M⁺ + 1] |
| 95 | 2-(3-cyclopentylpropanoyl)-{1,1-[3-(dimethylamino-(4-chlorophenyl)-methyl)-pentamethylene]-3,4-dihydro-1H-2,9-diazafluorene} | 532.3, 534.4 [M⁺ + 1] |
| 96 | 2-(cyclopropylcarbonyl)-{1,1-[3-(dimethylamino-(4-chlorophenyl)-methyl)-pentamethylene]-3,4-dihydro-1H-2,9-diazafluorene} | 476.3, 478.3 [M⁺ + 1] |
| 97 | 2-(methoxyacetyl)-{1,1-[3-(dimethylamino-(4-chlorophenyl)methyl)-pentamethylene]-3,4-dihydro-1H-2,9-diazafluorene} | 480.3, 482.3 [M⁺ + 1] |
| 98 | 2-(2-thienylacetyl)-{1,1-[3-(dimethylamino-(4-chlorophenyl)methyl)-pentamethylene]-3,4-dihydro-1H-2,9-diazafluorene} | 532.2, 534.2 [M⁺ + 1] |
| 99 | 2-(benzyloxyacetyl)-{1,1-[3-(dimethylamino-(4-chlorophenyl)methyl)-pentamethylene]-3,4-dihydro-1H-2,9-diazafluorene} | 556.3, 558.3 [M⁺ + 1] |
| 100 | 2-(2-ethylhexanoyl)-{1,1-[3-(dimethylamino-phenylmethyl)-pentamethylene]-3,4-dihydro-1H-2,9-diazafluorene} | 499.7 [M⁺ + 1] |
| 101 | 2-isobutyryl-{1,1-[3-(dimethylamino-phenylmethyl)-pentamethylene]-3,4-dihydro-1H-2,9-diazafluorene} | 443.6 [M⁺ + 1] |
| 102 | 2-propionyl-{1,1-[3-(dimethylamino-phenylmethyl)-pentamethylene]-3,4-dihydro-1H-2,9-diazafluorene} | 429.6 [M⁺ + 1] |
| 103 | 2-(1-benzothien-3-ylcarbonyl)-{1,1-[3-(dimethylamino-phenylmethyl)-pentamethylene]-3,4-dihydro-1H-2,9-diazafluorene} | 533.7 [M⁺ + 1] |
| 104 | 2-[(4-fluorophenyl)acetyl]-{1,1-[3-(dimethylamino-phenylmethyl)-pentamethylene]-3,4-dihydro-1H-2,9-diazafluorene} | 509.7 [M⁺ + 1] |
| 105 | 2-(3-chloro-1-benzothien-2-ylcarbonyl)-{1,1-[3-(dimethylamino-phenylmethyl)-pentamethylene]-3,4-dihydro-1H-2,9-diazafluorene} | 568.2 [M⁺ + 1] |
| 106 | 2-(2-ethylhexanoyl)-{1,1-[3-(dimethylamino-(4-fluorophenyl)methyl)-pentamethylene]-3,4-dihydro-1H-2,9-diazafluorene} | 517.7 [M⁺ + 1] |
| 107 | 2-isobutyryl-{1,1-[3-(dimethylamino-(4-fluorophenyl)methyl)-pentamethylene]-3,4-dihydro-1H-2,9-diazafluorene} | 461.6 [M⁺ + 1] |
| 108 | 2-propionyl-{1,1-[3-(dimethylamino-(4-fluorophenyl)methyl)-pentamethylene]-3,4-dihydro-1H-2,9-diazafluorene} | 447.6 [M⁺ + 1] |
| 109 | 2-cyclopentylcarbonyl-{1,1-[3-(dimethylamino-(4-fluorophenyl)methyl)-pentamethylene]-3,4-dihydro-1H-2,9-diazafluorene} | 487.7 [M⁺ + 1] |
| 110 | 2-[(4-fluorophenyl)acetyl]-{1,1-[3-(dimethylamino-(4-fluorophenyl)-methyl)-pentamethylene]-3,4-dihydro-1H-2,9-diazafluorene} | 527.7 [M⁺ + 1] |

-continued

| No. | Name | m/z |
|---|---|---|
| 111 | 2-(2-ethylhexanoyl)-{1,1-[3-(dimethylamino-(3-fluorophenyl)methyl)-pentamethylene]-3,4-dihydro-1H-2,9-diazafluorene} | 517.7 [M$^+$ + 1] |
| 112 | 2-isobutyryl-{1,1-[3-(dimethylamino-(3-fluorophenyl)methyl)-pentamethylene]-3,4-dihydro-1H-2,9-diazafluorene} | 461.6 [M$^+$ + 1] |
| 113 | 2-propionyl-{1,1-[3-(dimethylamino-(3-fluorophenyl)methyl)-pentamethylene]-3,4-dihydro-1H-2,9-diazafluorene} | 447.6 [M$^+$ + 1] |
| 114 | 2-(1-benzothien-3-ylcarbonyl)-{1,1-[3-(dimethylamino-(3-fluorophenyl)-methyl)-pentamethylene]-3,4-dihydro-1H-2,9-diazafluorene} | 551.7 [M$^+$ + 1] |
| 115 | 2-cyclopentylcarbonyl-{1,1-[3-(dimethylamino-(3-fluorophenyl)methyl)-pentamethylene]-3,4-dihydro-1H-2,9-diazafluorene} | 487.7 [M$^+$ + 1] |
| 116 | 2-[(4-fluorophenyl)acetyl]-{1,1-[3-(dimethylamino-(3-fluorophenyl)-methyl)-pentamethylene]-3,4-dihydro-1H-2,9-diazafluorene} | 527.7 [M$^+$ + 1] |
| 117 | 2-(3-chloro-1-benzothien-2-ylcarbonyl)-{1,1-[3-(dimethylamino-(3-fluoro-phenyl)methyl)-pentamethylene]-3,4-dihydro-1H-2,9-diazafluorene} | 586.2 [M$^+$ + 1], 588.2 |
| 118 | 2-(2-ethylhexanoyl)-{1,1-[3-(dimethylamino-(4-chlorophenyl)methyl)-pentamethylene]-3,4-dihydro-1H-2,9-diazafluorene} | 534.2 [M$^+$ + 1], 536.2 |
| 119 | 2-isobutyryl-{1,1-[3-(dimethylamino-(4-chlorophenyl)methyl)-pentamethylene]-3,4-dihydro-1H-2,9-diazafluorene} | 478.1 [M$^+$ + 1], 480.1 |
| 120 | 2-propionyl-{1,1-[3-(dimethylamino-(4-chlorophenyl)methyl)-pentamethylene]-3,4-dihydro-1H-2,9-diazafluorene} | 464.1 [M$^+$ + 1], 466.1 |
| 121 | 2-(1-benzothien-3-ylcarbonyl)-{1,1-[3-(dimethylamino-(4-chlorophenyl)-methyl)-pentamethylene]-3,4-dihydro-1H-2,9-diazafluorene} | 568.2 [M$^+$ + 1], 570.1 |
| 122 | 2-cyclopentylcarbonyl-{1,1-[3-(dimethylamino-(4-chlorophenyl)methyl)-pentamethylene]-3,4-dihydro-1H-2,9-diazafluorene} | 504.1 [M$^+$ + 1], 506.1 |
| 123 | 2-[(4-fluorophenyl)acetyl]-{1,1-[3-(dimethylamino-(4-chlorophenyl)-methyl)-pentamethylene]-3,4-dihydro-1H-2,9-diazafluorene} | 544.1 [M$^+$ + 1], 546.1 |
| 124 | 2-(3-chloro-1-benzothien-2-ylcarbonyl){1,1-[3-(dimethylamino-(4-chloro-phenyl)methyl)-pentamethylene]-3,4-dihydro-1H-2,9-diazafluorene} | 602.6 [M$^+$ + 1], 604.6, 606.6 |
| 125 | 2-cyclopentylcarbonyl-{1,1-[3-(dimethylamino-phenylmethyl)-pentamethylene]-3,4-dihydro-1H-2,9-diazafluorene} | 469.7 [M$^+$ + 1] |
| 126 | 2-[(3-methoxyphenyl)acetyl]-{1,1-[3-(dimethylamino-(3-fluorophenyl)-methyl)-pentamethylene]-3,4-dihydro-1H-2,9-diazafluorene} | 540.3 [M$^+$ + 1] |
| 127 | 2-(2-phenoxypropanoyl)-{1,1-[3-(dimethylamino-(3-fluorophenyl)-methyl)-pentamethylene]-3,4-dihydro-1H-2,9-diazafluorene} | 540.3 [M$^+$ + 1] |
| 128 | 2-[5-methylbenzothien-2-ylcarbonyl]-{1,1-[3-(dimethylamino-(3-fluoro-phenyl)methyl)-pentamethylene]-3,4-dihydro-1H-2,9-diazafluorene} | 566.3 [M$^+$ + 1] |
| 129 | 1-{1,1-[3-(dimethylamino-(3-fluorophenyl)methyl)-pentamethylene]-3,4-dihydro-1H-2,9-diazafluoren-2-yl}-3-methylbutan-1-one | 476.3 [M$^+$ + 1] |
| 130 | 1-{1,1-[3-(dimethylamino-(3-fluorophenyl)methyl)-pentamethylene]-3,4-dihydro-1H-2,9-diazafluoren-2-yl}-3-phenylbutan-1-one | 524.3 [M$^+$ + 1] |
| 131 | 2-(3-phenylpropanoyl)-{1,1-[3-(dimethylamino-(4-chlorophenyl)methyl)-pentamethylene]-3,4-dihydro-1H-2,9-diazafluorene} | 506.3 [M$^+$ + 1], 508.3 |
| 132 | 2-[(3-bromophenyl)acetyl]-{1,1-[3-(dimethylamino-(4-chlorophenyl)-methyl)-pentamethylene]-3,4-dihydro-1H-2,9-diazafluorene} | 556.3 [M$^+$ + 1], 558.3 |
| 133 | 2-(2-phenoxypropanoyl)-{1,1-[3-(dimethylamino-(4-chlorophenyl)-methyl)-pentamethylene]-3,4-dihydro-1H-2,9-diazafluorene} | 556.3 [M$^+$ + 1], 558.3 |
| 134 | 1-{1,1-[3-(dimethylamino-(4-chlorophenyl)methyl)-pentamethylene]-3,4-dihydro-1H-2,9-diazafluoren-2-yl}-3-methylbutan-1-one | 492.3 [M$^+$ + 1], 494.3 |
| 135 | (3-phenylpropanoyl)-1-{1,1-[3-(dimethylamino-(4-chlorophenyl)methyl)-pentamethylene]-3,4-dihydro-1H-2,9-diazafluorene} | 540.3 [M$^+$ + 1], 542.3 |
| 136 | 2-[(3-methoxyphenyl)acetyl]-{1,1-[3-(dimethylamino-phenylmethyl)-pentamethylene]-3,4-dihydro-1H-2,9-diazafluorene} | 522.3 [M$^+$ + 1] |
| 137 | 2-(2-phenoxypropanoyl)-{1,1-[3-(dimethylamino-phenylmethyl)-pentamethylene]-3,4-dihydro-1H-2,9-diazafluorene} | 522.3 [M$^+$ + 1] |
| 138 | 1-{1,1-[3-(dimethylamino-phenylmethyl)-pentamethylene]-3,4-dihydro-1H-2,9-diazafluoren-2-yl}-3-methylbutan-1-one | 458.3 [M$^+$ + 1] |
| 139 | 1-{1,1-[3-(dimethylamino-(4-fluorophenyl)methyl)-pentamethylene]-3,4-dihydro-1H-2,9-diazafluoren-2-yl}-2-ethylbutan-1-one | 490.3 [M$^+$ + 1] |
| 140 | 2-[(3-methoxyphenyl)acetyl]-{1,1-[3-(dimethylamino-(4-fluorophenyl)-methyl)-pentamethylene]-3,4-dihydro-1H-2,9-diazafluorene} | 540.3 [M$^+$ + 1] |
| 141 | 2-(2-phenoxypropanoyl)-{1,1-[3-(dimethylamino-(4-fluorophenyl)-methyl)-pentamethylene]-3,4-dihydro-1H-2,9-diazafluorene} | 540.3 [M$^+$ + 1] |
| 142 | 1-{1,1-[3-(dimethylamino-(4-fluorophenyl)methyl)-pentamethylene]-3,4-dihydro-1H-2,9-diazafluoren-2-yl}-3-phenylbutan-1-one | 524.3 [M$^+$ + 1] |

Investigations of the Activity of the Compounds According to the Invention

Method for Determination of the Affinity for the Human µ Opiate Receptor

The receptor affinity for the human µ opiate receptor is determined in a homogeneous set-up in microtitre plates. For this purpose, dilution series of the substances to be tested are incubated with a receptor membrane preparation (15-40 µg of protein/250 µl of incubation batch) of CHO-K1 cells which express the human µ opiate receptor (RB-HOM receptor membrane preparation from PerkinElmer Life Sciences, Zaventem, Belgium) in the presence of 1 nmol/l of the radioactive ligand [$^3$H]-naloxone (NET719, PerkinElmer Life Sciences, Zaventem, Belgium) and 1 mg of WGA-SPA-Beads (wheat germ agglutinin SPA beads from Amersham/Pharmacia, Freiburg, Germany) in a total volume of 250 µl for 90 minutes at room temperature. 50 mmol/l of Tris-HCl supplemented with 0.06% of bovine serum albumin are used as the incubation buffer. 100 µmol/l of naloxone are additionally added for determination of the non-specific binding. After the end of the ninety-minute incubation time, the microtitre plates are centrifuged for 20 minutes at 1,000 g and the radioactivity is measured in a β-counter (Microbeta-Trilum, PerkinElmer Wallac, Freiburg, Germany). The percentage displacement of the radioactive ligand from its binding to the human μ opiate receptor is determined at a concentration of the test substances of 1 μmol/l and stated as the percentage inhibition of the specific binding. Starting from the percentage displacement by various concentrations of the test substances, $IC_{50}$ inhibitory concentrations which cause a 50 percent displacement of the radioactive ligand are calculated. By conversion by means of the Cheng-Prusoff relationship, $K_i$ values for the test substances are obtained.

Inhibition of Noradrenaline (NA) and Serotonin (5HT) Reuptake

In order to be able to carry out these in vitro studies, synaptosomes are freshly isolated from areas of the rat brain. In each case a so-called "$P_2$" fraction prepared in accordance with the instruction of Gray and Whittaker (E. G. Gray and V. P. Whittaker (1962) J. Anat. 76, 79-88) is prepared. For the NA uptake, these vesicular particles are isolated from the hypothalamus of male rat brains.

A detailed description of the method can be found in the literature (M. Ch. Frink, H.-H. Hennies, W. Englberger, M. Haurand and B. Wilffert (1996) Arzneim.-Forsch./Drug Res. 46 (III), 11, 1029-1036).

Phenylquinone Writhing

The analgesic activity was investigated in the phenylquinone-induced writhing in mice (modified in accordance with I. C. Hendershot und J. Forsaith (1959) J. Pharmacol. Exp. Ther. 125, 237-240), Male NMRI mice weighing from 25 to 30 g were used for this. Groups of 10 animals per substance dose received 0.3 ml/mouse of a 0.02% strength aqueous solution of phenylquinone (phenylbenzoquinone, Sigma, Deisenhofen; preparation of the solution with the addition of 5% ethanol and storage in a water bath at 45° C.) administered intraperitoneally 10 minutes after intravenous administration of the test substances. The animals were placed individually in observation cages. The number of pain-induced stretching movements (so-called writhing reactions=straightening of the body with stretching of the rear extremities) was counted by means of a push-button counter 5 to 20 minutes after the administration of phenylquinone. Animals which receive only 5% strength Cremophor solution were also run as a control. All the substances were tested in the standard dosage of 10 mg/kg. The percentage inhibition (% inhibition) of the writhing reaction by a substance was calculated according to the following formula:

$$\% \text{ inhibition} = 100 - \frac{\text{writhing reactions of the treated animals}}{\text{writhing reactions of the control animals}} * 100$$

All the compounds according to the invention investigated showed a pronounced analgesic activity.

TABLE 1

Noradrenaline reuptake inhibition of compounds 18-21; 26-28; 35; 38; 53

| | X | $R^3$ | $R^5$ | $R^8$ | Noradrenaline reuptake, % inhibition [10 μM] |
|---|---|---|---|---|---|
| 18 | NH | 3-fluorophenyl | H | H | 58 |
| 19 | NH | phenyl | H | H | 65 |
| 20 | NH | phenethyl | H | H | 91 |
| 21 | NH | 2-thiophene | H | H | 50 |
| 26 | O | 3-fluorophenyl | H | H | 49 |
| 27 | O | phenyl | H | H | 64 |
| 28 | O | phenethyl | H | H | 52 |
| 35 | O | 4-fluorophenyl | F | H | 50 |
| 38 | O | 4-chlorophenyl | F | H | 59 |
| 53 | O | phenyl | F | $CH_3$ | 47 |

TABLE 2

5HT uptake inhibition of compounds 17-22; 25-30; 35; 37; 38; 40; 42; 51-54

| | X | $R^3$ | $R^5$ | $R^8$ | Serotonin reuptake, % inhibition [10 μM] |
|---|---|---|---|---|---|
| 17 | NH | 4-fluorophenyl | H | H | 83 |
| 18 | NH | 3-fluorophenyl | H | H | 64 |
| 19 | NH | phenyl | H | H | 91 |
| 20 | NH | phenethyl | H | H | 84 |
| 21 | NH | 2-thiophene | H | H | 72 |
| 22 | NH | 4-chlorophenyl | H | H | 76 |
| 25 | O | 4-fluorophenyl | H | H | 68 |
| 26 | O | 3-fluorophenyl | H | H | 59 |
| 27 | O | phenyl | H | H | 73 |
| 28 | O | phenethyl | H | H | 57 |
| 29 | O | 2-thiophene | H | H | 45 |
| 30 | O | 4-chlorophenyl | H | H | 56 |
| 35 | O | 4-fluorophenyl | F | H | 55 |
| 37 | O | phenyl | F | H | 68 |
| 38 | O | 4-chlorophenyl | F | H | 57 |
| 40 | O | 4-fluorophenyl | $CH_3$ | $CH_3$ | 47 |
| 42 | O | phenyl | $CH_3$ | $CH_3$ | 64 |
| 51 | O | 4-fluorophenyl | F | $CH_3$ | 39 |
| 52 | O | 3-fluorophenyl | F | $CH_3$ | 68 |
| 53 | O | phenyl | F | $CH_3$ | 60 |
| 54 | O | phenethyl | F | $CH_3$ | 55 |

TABLE 3

μ affinity of compounds 17-22; 25-30; 35-38; 40-44; 51-55

| | X | $R^3$ | $R^5$ | $R^8$ | μ opioid receptor [1 μM], % inhibition | μ opioid receptor, Ki [μM] |
|---|---|---|---|---|---|---|
| 17 | NH | 4-fluorophenyl | H | H | 46 | n.d. |
| 18 | NH | 3-fluorophenyl | H | H | 74 | 0.260 |
| 19 | NH | phenyl | H | H | 81 | 0.180 |
| 20 | NH | phenethyl | H | H | 97 | 0.034 |
| 21 | NH | 2-thiophene | H | H | 62 | n.d. |
| 22 | NH | 4-chlorophenyl | H | H | 33 | n.d. |
| 25 | O | 4-fluorophenyl | H | H | 86 | 0.350 |
| 26 | O | 3-fluorophenyl | H | H | 94 | 0.033 |
| 27 | O | phenyl | H | H | 99 | 0.026 |
| 28 | O | phenethyl | H | H | 92 | 0.110 |
| 29 | O | 2-thiophene | H | H | 99 | 0.015 |
| 30 | O | 4-chlorophenyl | H | H | 84 | 0.170 |
| 35 | O | 4-fluorophenyl | F | H | 98 | 0.067 |
| 36 | O | 3-fluorophenyl | F | H | 102 | 0.046 |
| 37 | O | phenyl | F | H | 74 | 0.037 |
| 38 | O | 4-chlorophenyl | F | H | 84 | 0.260 |
| 40 | O | 4-fluorophenyl | $CH_3$ | $CH_3$ | 68 | n.d. |
| 41 | O | 3-fluorophenyl | $CH_3$ | $CH_3$ | 88 | 0.300 |
| 42 | O | phenyl | $CH_3$ | $CH_3$ | 101 | 0.029 |
| 43 | O | phenethyl | $CH_3$ | $CH_3$ | 42 | n.d. |

TABLE 3-continued

μ affinity of compounds 17-22; 25-30; 35-38; 40-44; 51-55

|    | X | $R^3$ | $R^5$ | $R^8$ | μ opioid receptor [1 μM], % inhibition | μ opioid receptor, Ki [μM] |
|----|---|-------|-------|-------|----------------------------------------|----------------------------|
| 44 | O | 4-chlorophenyl | $CH_3$ | $CH_3$ | 72 | 0.490 |
| 51 | O | 4-fluorophenyl | F | $CH_3$ | 46 | n.d. |
| 52 | O | 3-fluorophenyl | F | $CH_3$ | 53 | n.d. |
| 53 | O | phenyl | F | $CH_3$ | 97 | 0.082 |
| 54 | O | phenethyl | F | $CH_3$ | 21 | n.d. |
| 55 | O | 4-chlorophenyl | F | $CH_3$ | 58 | n.d. |

TABLE 4

Phenylquinone writhing

| Example no. | % inhibition of the writhing reaction (dosage in mg/kg intravenously) |
|-------------|-----------------------------------------------------------------------|
| 17 | 52 (10) |
| 20 | 45 (10) |
| 27 | 53 (10) |
| 29 | 73 (10) |
| 30 | 45 (10) |
| 41 | 40 (10) |
| 44 | 48 (10) |

Affinity for the μ opioid receptor of the compounds prepared via automated synthesis (single measurements at a test concentration of 1 μM)

| | μ opioid receptor [1 μmol], % inhibition |
|---|---|
| 56 | 36 |
| 57 | 55 |
| 58 | 50 |
| 59 | 29 |
| 60 | 26 |
| 61 | 6 |
| 62 | 12 |
| 63 | 29 |
| 64 | 15 |
| 65 | 17 |
| 66 | 26 |
| 67 | 25 |
| 68 | 19 |
| 69 | 26 |
| 70 | 31 |
| 71 | — |
| 72 | 24 |
| 73 | 24 |
| 74 | 37 |
| 75 | 13 |
| 76 | 15 |
| 77 | 17 |
| 78 | 11 |
| 79 | 4 |
| 80 | 41 |
| 81 | 0 |
| 82 | 31 |
| 83 | 50 |
| 84 | 41 |
| 85 | 50 |
| 86 | 12 |
| 87 | — |
| 88 | 11 |
| 89 | 10 |
| 90 | — |
| 91 | 25 |
| 92 | 22 |
| 93 | 19 |
| 94 | 32 |
| 95 | 18 |
| 96 | 18 |
| 97 | 20 |
| 98 | 21 |
| 99 | 35 |
| 100 | 65 |
| 101 | 74 |
| 102 | 55 |
| 103 | 13 |
| 104 | 39 |
| 105 | — |
| 106 | — |
| 107 | — |
| 108 | — |
| 109 | 21 |
| 110 | 14 |
| 111 | 13 |
| 112 | — |
| 113 | 13 |
| 114 | — |
| 115 | — |
| 116 | 20 |
| 117 | — |
| 118 | 35 |
| 119 | 40 |
| 120 | 29 |
| 121 | — |
| 122 | — |
| 123 | 20 |
| 124 | — |
| 125 | 29 |
| 126 | 50 |
| 127 | 55 |
| 128 | 16 |
| 129 | 74 |
| 130 | 49 |
| 131 | 51 |
| 132 | 65 |
| 133 | 71 |
| 134 | 47 |
| 135 | 38 |
| 136 | 75 |
| 137 | 68 |
| 138 | 58 |
| 139 | 25 |
| 140 | 47 |
| 141 | 47 |
| 142 | 30 |

The foregoing description and examples have been set forth merely to illustrate the invention and are not intended to be limiting. Since modifications of the disclosed embodiments incorporating the spirit and substance of the invention may occur to persons skilled in the art, the invention should be construed broadly to include all variations within the scope of the appended claims and equivalents thereof.

The invention claimed is:

1. A spirocyclic cyclohexane compound corresponding to formula I

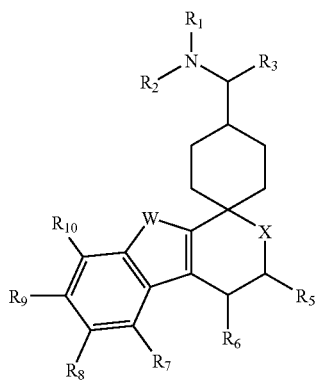

wherein
R¹ and R² each independently denote H; $C_{1-6}$-alkyl, in each case saturated or unsaturated, branched or unbranched, with the proviso that R¹ and R² are not simultaneously H, or R¹ and R² together denote $CH_2CH_2OCH_2CH_2$, $CH_2CH_2NR^{11}CH_2CH_2$ or $(CH_2)_{3-6}$, wherein
R¹¹ denotes H; $C_{1-5}$-alkyl or $C_{3-8}$-cycloalkyl, in each case saturated or unsaturated, branched or unbranched, mono- or polysubstituted or unsubstituted; aryl or heteroaryl, in each case mono- or polysubstituted or unsubstituted; or aryl or $C_{3-8}$-cycloalkyl or heteroaryl, bonded via a $C_{1-3}$-alkyl group and in each case unsubstituted or mono- or polysubstituted;

R³ represents aryl, heteroaryl, in each case unsubstituted or mono- or polysubstituted; aryl or heteroaryl linked via a $C_{1-3}$-alkyl group and in each case unsubstituted or mono- or polysubstituted; $C_{3-8}$-cycloalkyl or $C_{1-8}$-alkyl, unsubstituted or mono- or polysubstituted;

W represents NR⁴, O or S, wherein
R⁴ represents H; $C_{1-5}$-alkyl, saturated or unsaturated, branched or unbranched, unsubstituted or mono- or polysubstituted; aryl or heteroaryl, in each case substituted or unsubstituted; aryl, heteroaryl or cycloalkyl bonded via a $C_{1-3}$-alkyl group and in each case mono- or polysubstituted or unsubstituted; $COR^{12}$; $CSR^{12}$; or $SO_2R^{12}$, wherein
R¹² denotes H; $C_{1-8}$-alkyl, in each case saturated or unsaturated, branched or unbranched, mono- or polysubstituted or unsubstituted; $C_{3-8}$-cycloalkyl, in each case saturated or unsaturated, mono- or polysubstituted or unsubstituted; aryl or heteroaryl, in each case mono- or polysubstituted or unsubstituted; aryl, $C_{3-8}$-cycloalkyl or heteroaryl bonded via $C_{1-3}$-alkyl and in each case mono- or polysubstituted or unsubstituted; $(CHR^a)_qOR^{13}$, q=0, 1 or 2 and $R^a$=H, methyl or ethyl; or $NR^{14}R^{15}$;

R⁵ represents H; $C_{1-5}$-alkyl, saturated or unsaturated, branched or unbranched, unsubstituted or mono- or polysubstituted; $COOR^{13}$; $CONR^{13}$; $OR^{13}$; $C_{3-8}$-cycloalkyl, saturated or unsaturated, unsubstituted or mono- or polysubstituted; aryl or heteroaryl, unsubstituted or mono- or polysubstituted; or aryl, $C_{3-8}$-cycloalkyl or heteroaryl bonded via $C_{1-3}$-alkyl and unsubstituted or mono- or polysubstituted;

R⁶ represents H; $OR^{13}$; $COOR^{13}$; $NR^{14}R^{15}$; $C_{1-5}$-alkyl, saturated or unsaturated, branched or unbranched, unsubstituted or mono- or polysubstituted; $C_{3-8}$-cycloalkyl, saturated or unsaturated, unsubstituted or mono- or polysubstituted; phenyl; or aryl or heteroaryl bonded via $C_{1-3}$-alkyl;

R⁷, R⁸, R⁹ and R¹⁰ each independently represent H, F, Cl, Br, $NO_2$, $CF_3$, $OR^{13}$, CN, $COOR^{13}$, $NR^{14}R^{15}$; $C_{1-5}$-alkyl, phenyl or benzyl;
wherein
R¹³ denotes H; $C_{1-5}$-alkyl, in each case saturated or unsaturated, branched or unbranched, unsubstituted or mono- or polysubstituted; $C_{3-8}$-cycloalkyl, in each case saturated or unsaturated, unsubstituted or mono- or polysubstituted; aryl or heteroaryl, unsubstituted or mono- or polysubstituted; or aryl, $C_{3-8}$-cycloalkyl or heteroaryl bonded via $C_{1-3}$-alkyl and unsubstituted or mono- or polysubstituted;
R¹⁴ and R¹⁵ each independently denote H or $C_{1-5}$-alkyl, or
R¹⁴ and R¹⁵ together form $CH_2CH_2OCH_2CH_2$, $CH_2CH_2NR^{16}CH_2CH_2$ or $(CH_2)_{3-6}$, wherein
R¹⁶ denotes H; $C_{1-5}$-alkyl, saturated or unsaturated; and X represents O, S, SO, $SO_2$ or $NR^{17}$; wherein
R¹⁷ represents H; $C_{1-5}$-alkyl, saturated or unsaturated, branched or unbranched, in each case mono- or polysubstituted or unsubstituted; $COR^{12}$ or $SO_2R^{12}$;

or a salt thereof with a physiologically acceptable acid.

2. A compound as claimed in claim 1, wherein said compound is in the form of an isolated stereoisomer.

3. A compound as claimed in claim 1, wherein said compound is in the form of a mixture of stereoisomers in any mixing ratio.

4. A compound as claimed in claim 1, wherein said compound is in the form of a racemic mixture.

5. A compound as claimed in claim 1, wherein R¹ and R² each independently denote H or $C_{1-5}$-alkyl, with the proviso that R¹ and R² are not simultaneously H, or R¹ and R² together denote $CH_2CH_2OCH_2CH_2$, or $(CH_2)_{3-5}$.

6. A compound as claimed in claim 5, wherein R¹ and R² each denote $CH_3$.

7. A compound as claimed in claim 1, wherein R³ denotes phenyl or thienyl, in each case unsubstituted or mono- or polysubstituted by F, Cl, CN, $NO_2$, SH, S—$C_{1-6}$-alkyl, OH, O—$C_{1-6}$-alkyl, $CO_2H$, $CO_2$—$C_{1-6}$-alkyl, $CF_3$, or $C_{1-6}$-alkyl; or
phenyl bonded via a $C_{1-3}$-alkyl chain and in each case unsubstituted or mono- or polysubstituted by F, Cl, CN, $NO_2$, SH, S—$C_{1-6}$-alkyl, OH, O—$C_{1-6}$-alkyl, $CO_2H$, $CO_2$—$C_{1-6}$-alkyl, $CF_3$, or $C_{1-6}$-alkyl.

8. A compound as claimed in claim 7, wherein R³ denotes phenyl unsubstituted or monosubstituted by Cl or F, phenethyl or thienyl.

9. A compound as claimed in claim 1, wherein R⁵ denotes H or $CH_3$.

10. A compound as claimed in claim 1, wherein R⁶ denotes H.

11. A compound as claimed in claim 1, wherein:
R⁸ and R⁹ each independently denote H, $C_{1-5}$-alkyl, F, Cl, Br, I, OH, $OCH_3$, COOH, $COOCH_3$, $NH_2$, $NHCH_3$, $N(CH_3)_2$ or $NO_2$; and
R¹⁰ and R⁷ each denote H.

12. A compound as claimed in claim 11, wherein R³ denotes H, F or $CH_3$; and
R⁷, R⁹ and R¹⁰ each denote H.

13. A compound as claimed in claim 1, wherein R¹⁷ denotes H or $COR^{12}$.

14. A compound as claimed in claim 13, wherein R¹² represents:

phenyl, phenethyl, phenethenyl, 1-methyl-phenethenyl or benzyl, each unsubstituted or mono- or polysubstituted by F, Cl, Br, I, CN, NH$_2$, NH—C$_{1-6}$-alkyl, NH—C$_{1-6}$-alkyl-OH, N(C$_{1-6}$-alkyl)$_2$, N(C$_{1-6}$-alkyl-OH)$_2$, NO$_2$, SH, S—C$_{1-6}$-alkyl, OH, O—C$_{1-6}$-alkyl, O—C$_{1-6}$-alkyl-OH, C(=O)C$_{1-6}$-alkyl, CO$_2$H, CO$_2$—C$_{1-6}$-alkyl, CF$_3$, or C$_{1-6}$-alkyl;

thienyl or benzothienyl, optionally bonded via a CH$_2$ or a CH$_2$CH$_2$ chain, and in each case unsubstituted or mono- or polysubstituted by F, Cl, Br, I, CN, NH$_2$, NH—C$_{1-6}$-alkyl, NH—C$_{1-6}$-alkyl-OH, N(C$_{1-6}$-alkyl)$_2$, N(C$_{1-6}$-alkyl-OH)$_2$, NO$_2$, SH, S—C$_{1-6}$-alkyl, OH, O—C$_{1-6}$-alkyl, O—C$_{1-6}$-alkyl-OH, C(=O)C$_{1-6}$-alkyl, CO$_2$H, CO$_2$—C$_{1-6}$-alkyl, CF$_3$, or C$_{1-6}$-alkyl;

cyclopropyl, cyclobutyl, cyclopentyl or cyclohexyl, optionally bonded via a CH$_2$ or a CH$_2$CH$_2$ chain, and in each case unsubstituted or mono- or polysubstituted by F, Cl, Br, —CN, NH$_2$, NH—C$_{1-6}$-alkyl, NH—C$_{1-6}$-alkyl-OH, C$_{1-6}$-alkyl, N(C$_{1-6}$-alkyl)$_2$, N(C$_{1-6}$-alkyl-OH)$_2$, NO$_2$, SH, S—C$_{1-6}$-alkyl, S-benzyl, O—C$_{1-6}$-alkyl, OH, O—C$_{1-6}$-alkyl-OH, =O, O-benzyl, C(=O)C$_{1-6}$-alkyl, CO$_2$H, CO$_2$—C$_{1-6}$-alkyl or benzyl; or (CHR$^a$)$_q$OR$^{13}$, where q=1 or 2, and R$^a$=H or methyl.

15. A compound as claimed in claim 1, selected from the group consisting of:

(17) 1,1-[3-(dimethylamino-(4-fluorophenyl)methyl)-pentamethylene]-3,4-dihydro-1H-2,9-diazafluorene;

(18) 1,1-[3-(dimethylamino-(3-fluorophenyl)methyl)-pentamethylene]-3,4-dihydro-1H-2,9-diazafluorene;

(19) 1,1-[3-(dimethylamino-phenylmethyl)-pentamethylene]-3,4-dihydro-1H-2,9-diazafluorene;

(20) 1,1-[3-(dimethylamino-(phenylethyl)-methyl)-pentamethylene]-3,4-dihydro-1H-2,9-diazafluorene citrate;

(21) 1,1-[3-(dimethylamino-(thiophen-2-yl)-methyl)-pentamethylene]-3,4-dihydro-1H-2,9-diazafluorene;

(22) 1,1-[3-(4-chlorophenyl-(dimethylamino)-methyl)-pentamethylene]-3,4-dihydro-1H-2,9-diazafluorene;

(23) cyclohexyl{1,1-[3-(dimethylamino-(4-fluorophenyl)-methyl)-pentamethylene]-3,4-dihydro-1H-2,9-diazafluoren-2-yl}methanone;

(24) phenyl{1,1-[3-(dimethylamino-(4-fluorophenyl)-methyl)-pentamethylene]-3,4-dihydro-1H-2,9-diazafluoren-2-yl}methanone

(25) 1,1-[3-(dimethylamino-(4-fluorophenyl)-methyl)-pentamethylene]-1,3,4,9-tetrahydro-pyrano[3,4-b]indole

(26) 1,1-[3-(dimethylamino-(3-fluorophenyl)-methyl)-pentamethylene]-1,3,4,9-tetrahydro-pyrano[3,4-b]indole

(27) 1,1-[3-(dimethylamino-(phenyl)-methyl)-pentamethylene]-1,3,4,9-tetrahydropyrano[3,4-b]indole citrate

(28) 1,1-[3-(dimethylamino-(phenylethyl)-methyl)-pentamethylene]-1,3,4,9-tetrahydropyrano[3,4-b]indole

(29) 1,1-[3-(dimethylamino-(thiophen-2-yl)-methyl)-pentamethylene]-1,3,4,9-tetrahydro-pyrano[3,4-b]indole

(30) 1,1-[3-(dimethylamino-(4-chlorophenyl)-methyl)-pentamethylene]-1,3,4,9-tetrahydro-pyrano[3,4-b]indole

(35) 6-fluoro-1,1-[3-(dimethylamino-(4-fluorophenyl)-methyl)-pentamethylene]-1,3,4,9-tetrahydropyrano[3,4-b]indole

(36) 6-fluoro-1,1-[3-(dimethylamino-(3-fluorophenyl)-methyl)-pentamethylene]-1,3,4,9-tetrahydropyrano[3,4-b]indole

(37) 6-fluoro-1,1-[3-(dimethylamino-(phenyl)-methyl)-pentamethylene]-1,3,4,9-tetrahydro-pyrano[3,4-b]indole

(38) 6-fluoro-1,1-[3-(dimethylamino-(4-chlorophenyl)-methyl)-pentamethylene]-1,3,4,9-tetrahydropyrano[3,4-b]indole

(40) 3,6-dimethyl-1,1-[3-(dimethylamino-(4-fluorophenyl)-methyl)-pentamethylene]-1,3,4,9-tetrahydropyrano[3,4-b]indole

(41) 3,6-dimethyl-1,1-[3-(dimethylamino-(3-fluorophenyl)-methyl)-pentamethylene]-1,3,4,9-tetrahydropyrano[3,4-b]indole

(42) 3,6-dimethyl-1,1-[3-(dimethylamino-(phenyl)-methyl)-pentamethylene]-1,3,4,9-tetrahydropyrano[3,4-b]indole citrate

(43) 3,6-dimethyl-1,1-[3-(dimethylamino-(phenylethyl)-methyl)-pentamethylene]-1,3,4,9-tetrahydropyrano[3,4-b]indole

(44) 3,6-dimethyl-1,1-[3-(dimethylamino-(4-chlorophenyl)-methyl)-pentamethylene]-1,3,4,9-tetrahydropyrano[3,4-b]indole

(51) 6-fluoro-3-methyl-1,1-[3-(dimethylamino-(4-fluorophenyl)-methyl)-pentamethylene]-1,3,4,9-tetrahydropyrano[3,4-b]indole

(52) 6-fluoro-3-methyl-1,1-[3-(dimethylamino-(3-fluorophenyl)-methyl)-pentamethylene]-1,3,4,9-tetrahydropyrano[3,4-b]indole

(53) 6-fluoro-3-methyl-1,1-[3-(dimethylamino-(phenyl)-methyl)-pentamethylene]-1,3,4,9-tetrahydropyrano[3,4-b]indole

(54) 6-fluoro-3-methyl-1,1-[3-(dimethylamino-(phenylethyl)-methyl)-pentamethylene]-1,3,4,9-tetrahydropyrano[3,4-b]indole

(55) 6-fluoro-3-methyl-1,1-[3-(dimethylamino-(4-chlorophenyl)-methyl)-pentamethylene]-1,3,4,9-tetrahydropyrano[3,4-b]indole

(56) 1-{1,1-[3-(dimethylamino-phenylmethyl)-pentamethylene]-3,4-dihydro-1H-2,9-diazafluoren-2-yl}-3,3-dimethylbutan-1-one

(57) 2-[(3,4-dimethoxyphenyl)acetyl]-{1,1-[3-(dimethylamino-phenylmethyl)-pentamethylene]-3,4-dihydro-1H-2,9-diazafluorene}

(58) 1-{1,1-[3-(dimethylamino-phenylmethyl)-pentamethylene]-3,4-dihydro-1H-2,9-diazafluoren-2-yl}-2-methyl-3-phenylprop-2-en-1-one

(59) 2-(cyclohexylcarbonyl)-{1,1-[3-(dimethylamino-phenylmethyl)-pentamethylene]-3,4-dihydro-1H-2,9-diazafluorene}

(60) 2-[(4-chlorophenoxy)acetyl]-{1,1-[3-(dimethylamino-phenylmethyl)-pentamethylene]-3,4-dihydro-1H-2,9-diazafluorene}

(61) 1-{1,1-[3-(dimethylamino-phenylmethyl)-pentamethylene]-3,4-dihydro-1H-2,9-diazafluoren-2-yl}-3-(2-chlorophenyl)prop-2-en-1-one

(62) 1-{1,1-[3-(dimethylamino-(4-fluorophenyl)methyl)-pentamethylene]-3,4-dihydro-1H-2,9-diazafluoren-2-yl}-3,3-dimethylbutan-1-one

(63) 2-[(3,4-dimethoxyphenyl)acetyl]-{1,1-[3-(dimethylamino-(4-fluorophenyl)methyl)-pentamethylene]-3,4-dihydro-1H-2,9-diazafluorene}

(64) 1-{1,1-[3-(dimethylamino-(4-fluorophenyl)methyl)-pentamethylene]-3,4-dihydro-1H-2,9-diazafluoren-2-yl}-2-methyl-3-phenylprop-2-en-1-one

(65) 2-[(4-chlorophenoxy)acetyl]-{1,1-[3-(dimethylamino-(4-fluorophenyl)methyl)-pentamethylene]-3,4-dihydro-1H-2,9-diazafluorene}

(66) 1-{1,1-[3-(dimethylamino-(3-fluorophenyl)methyl)-pentamethylene]-3,4-dihydro-1H-2,9-diazafluoren-2-yl}-3,3-dimethylbutan-1-one
(67) 2-[(3,4-dimethoxyphenyl)acetyl]-{1,1-[3-(dimethylamino-(3-fluorophenyl)methyl)-pentamethylene]-3,4-dihydro-1H-2,9-diazafluorene}
(68) 1-{1,1-[3-(dimethylamino-(3-fluorophenyl)methyl)-pentamethylene]-3,4-dihydro-1H-2,9-diazafluoren-2-yl}-2-methyl-3-phenylprop-2-en-1-one
(69) 2-(cyclohexylcarbonyl)-{1,1-[3-(dimethylamino-(3-fluorophenyl)methyl)-pentamethylene]-3,4-dihydro-1H-2,9-diazafluorene}
(70) 2-[(4-chlorophenoxy)acetyl]-{1,1-[3-(dimethylamino-(3-fluorophenyl)methyl)-pentamethylene]-3,4-dihydro-1H-2,9-diazafluorene}
(71) 2-(1-benzothien-2-ylcarbonyl)-{1,1-[3-(dimethylamino-(3-fluorophenyl)methyl)-pentamethylene]-3,4-dihydro-1H-2,9-diazafluorene}
(72) 1-{1,1-[3-(dimethylamino-(3-fluorophenyl)methyl)-pentamethylene]-3,4-dihydro-1H-2,9-diazafluoren-2-yl}-3-(2-chlorophenyl)prop-2-en-1-one
(73) 1-{1,1-[3-(dimethylamino-(4-chlorophenyl)methyl)-pentamethylene]-3,4-dihydro-1H-2,9-diazafluoren-2-yl}-3,3-dimethylbutan-1-one
(74) 2-[(3,4-dimethoxyphenyl)acetyl]-{1,1-[3-(dimethylamino-(4-chlorophenyl)methyl)-pentamethylene]-3,4-dihydro-1H-2,9-diazafluorene}
(75) 1-{1,1-[3-(dimethylamino-(4-chlorophenyl)methyl)-pentamethylene]-3,4-dihydro-1H-2,9-diazafluoren-2-yl}-2-methyl-3-phenylprop-2-en-1-one
(76) 2-(cyclohexylcarbonyl)-{1,1-[3-(dimethylamino-(4-chlorophenyl)methyl)-pentamethylene]-3,4-dihydro-1H-2,9-diazafluorene}
(77) 2-[(4-chlorophenoxy)acetyl]-{1,1-[3-(dimethylamino-(4-chlorophenyl)methyl)-pentamethylene]-3,4-dihydro-1H-2,9-diazafluorene}
(78) 2-(1-benzothien-2-ylcarbonyl)-{1,1-[3-(dimethylamino-(4-chlorophenyl)methyl)-pentamethylene]-3,4-dihydro-1H-2,9-diazafluorene}
(79) 2-acetyl-{1,1-[3-(dimethylamino-phenylmethyl)-pentamethylene]-3,4-dihydro-1H-2,9-diazafluorene}
(80) 1-{1,1-[3-(dimethylamino-phenylmethyl)-pentamethylene]-3,4-dihydro-1H-2,9-diazafluoren-2-yl}-3-phenylprop-2-en-1-one
(81) 2-(methoxyacetyl)-{1,1-[3-(dimethylamino-phenylmethyl) -pentamethylene]-3,4-dihydro-1H-2,9-diazafluorene}
(82) 2-(2-thienylacetyl)-{1,1-[3-(dimethylamino -phenylmethyl)-pentamethylene]-3,4-dihydro-1H-2,9-diazafluorene}
(83) 2-(benzyloxyacetyl)-{1,1-[3-(dimethylamino-phenylmethyl) -pentamethylene]-3,4-dihydro-1H-2,9-diazafluorene}
(84) acetyl-{1,1-[3-(dimethylamino-(4-fluorophenyl)methyl) -pentamethylene]-3,4-dihydro-1H-2,9-diazafluorene}
(85) 2-(3-cyclopentylpropanoyl)-{1,1-[3-(dimethylamino-(4-fluorophenyl)methyl)-pentamethylene]-3,4-dihydro-1H-2,9-diazafluorene}
(86) 1-{1,1-[3-(dimethylamino-(4-fluorophenyl)methyl)-pentamethylene]-3,4-dihydro-1H-2,9-diazafluoren-2-yl}-3-phenylprop-2-en-1-one
(87) 2-(2-thienylacetyl)-{1,1-[3-(dimethylamino-(4-fluorophenyl)methyl)-pentamethylene]-3,4-dihydro-1H-2,9-diazafluorene}
(88) 2-(benzyloxyacetyl)-{1,1-[3-(dimethylamino-(4-fluorophenyl)methyl)-pentamethylene]-3,4-dihydro-1H-2,9-diazafluorene}
(89) acetyl-{1,1-[3-(dimethylamino-(3-fluorophenyl)methyl) -pentamethylene]-3,4-dihydro-1H-2,9-diazafluorene}
(90) 2-(3-cyclopentylpropanoyl)-{1,1-[3-(dimethylamino-(3-fluorophenyl)methyl)-pentamethylene]-3,4-dihydro-1H-2,9-diazafluorene}
(91) 2-(cyclopropylcarbonyl)-{1,1-[3-(dimethylamino-(3-fluorophenyl)methyl)-pentamethylene]-3,4-dihydro-1H-2,9-diazafluorene}
(92) 2-(methoxyacetyl)-{1,1-[3-(dimethylamino-(3-fluorophenyl)methyl)-pentamethylene]-3,4-dihydro-1H-2,9-diazafluorene}
(93) 2-(2-thienylacetyl)-{1,1-[3-(dimethylamino-(3-fluorophenyl)methyl)-pentamethylene]-3,4-dihydro-1H-2,9-diazafluorene}
(94) 2-(benzyloxyacetyl)-{1,1-[3-(dimethylamino-(3-fluorophenyl)methyl)-pentamethylene]-3,4-dihydro-1H-2,9-diazafluorene}
(95) 2-(3-cyclopentylpropanoyl)-{1,1-[3-(dimethylamino-(4-chlorophenyl)methyl)-pentamethylene]-3,4-dihydro-1H-2,9-diazafluorene}
(96) 2-(cyclopropylcarbonyl)-{1,1-[3-(dimethylamino-(4-chlorophenyl)methyl)-pentamethylene]-3,4-dihydro-1H-2,9-diazafluorene}
(97) 2-(methoxyacetyl)-{1,1-[3-(dimethylamino-(4-chlorophenyl)methyl)-pentamethylene]-3,4-dihydro-1H-2,9-diazafluorene}
(98) 2-(2-thienylacetyl)-{1,1-[3-(dimethylamino-(4-chlorophenyl)methyl)-pentamethylene]-3,4-dihydro-1H-2,9-diazafluorene}
(99) 2-(benzyloxyacetyl)-{1,1-[3-(dimethylamino-(4-chlorophenyl)methyl)-pentamethylene]-3,4-dihydro-1H-2,9-diazafluorene}
(100) 2-(2-ethylhexanoyl)-{1,1-[3-(dimethylamino -phenylmethyl)-pentamethylene]-3,4-dihydro-1H-2,9-diazafluorene}
(101) 2-isobutyryl-{1,1-[3-(dimethylamino-phenylmethyl) -pentamethylene]-3,4-dihydro-1H-2,9-diazafluorene}
(102) 2-propionyl-{1,1-[3-(dimethylamino-phenylmethyl) -pentamethylene]-3,4-dihydro-1H-2,9-diazafluorene}
(103) 2-(1-benzothien-3-ylcarbonyl)-{1,1-[3-(dimethylamino-phenylmethyl)-pentamethylene]-3,4-dihydro-1H-2,9-diazafluorene}
(104) 2-[(4-fluorophenyl)acetyl]-{1,1-[3-(dimethylamino-phenylmethyl)-pentamethylene]-3,4-dihydro-1H-2,9-diazafluorene}
(105) 2-(3-chloro-1-benzothien-2-ylcarbonyl)-{1,1-[3-(dimethylamino-phenylmethyl)-pentamethylene]-3,4-dihydro-1H-2,9-diazafluorene}
(106) 2-(2-ethylhexanoyl)-{1,1-[3-(dimethylamino-(4-fluorophenyl)methyl)-pentamethylene]-3,4-dihydro-1H-2,9-diazafluorene}
(107) 2-isobutyryl-{1,1-[3-(dimethylamino-(4-fluorophenyl)methyl)-pentamethylene]-3,4-dihydro-1H-2,9-diazafluorene}
(108) 2-propionyl-{1,1-[3-(dimethylamino-(4-fluorophenyl)methyl)-pentamethylene]-3,4-dihydro-1H-2,9-diazafluorene}
(109) 2-cyclopentylcarbonyl-{1,1-[3-(dimethylamino-(4-fluorophenyl)methyl)-pentamethylene]-3,4-dihydro-1H-2,9-diazafluorene}

(110) 2-[(4-fluorophenyl)acetyl]-{1,1-[3-(dimethylamino-(4-fluorophenyl)methyl)-pentamethylene]-3,4-dihydro-1H-2,9-diazafluorene}

(111) 2-(2-ethylhexanoyl)-{1,1-[3-(dimethylamino-(3-fluorophenyl)methyl)-pentamethylene]-3,4-dihydro-1H-2,9-diazafluorene}

(112) 2-isobutyryl-{1,1-[3-(dimethylamino-(3-fluorophenyl)methyl)-pentamethylene]-3,4-dihydro-1H-2,9-diazafluorene}

(113) 2-propionyl-{1,1-[3-(dimethylamino-(3-fluorophenyl)methyl)-pentamethylene]-3,4-dihydro-1H-2,9-diazafluorene}

(114) 2-(1-benzothien-3-ylcarbonyl)-{1,1-[3-(dimethylamino-(3-fluorophenyl)methyl)-pentamethylene]-3,4-dihydro-1H-2,9-diazafluorene}

(115) 2-cyclopentylcarbonyl-{1,1-[3-(dimethylamino-(3-fluorophenyl)methyl)-pentamethylene]-3,4-dihydro-1H-2,9-diazafluorene}

(116) 2-[(4-fluorophenyl)acetyl]-{1,1-[3-(dimethylamino-(3-fluorophenyl)methyl)-pentamethylene]-3,4-dihydro-1H-2,9-diazafluorene}

(117) 2-(3-chloro-1-benzothien-2-ylcarbonyl)-{1,1-[3-(dimethylamino-(3-fluorophenyl)methyl)-pentamethylene]-3,4-dihydro-1H-2,9-diazafluorene}

(118) 2-(2-ethylhexanoyl)-{1,1-[3-(dimethylamino-(4-chlorophenyl)methyl)-pentamethylene]-3,4-dihydro-1H-2,9-diazafluorene}

(119) 2-isobutyryl-{1,1-[3-(dimethylamino-(4-chlorophenyl)methyl)-pentamethylene]-3,4-dihydro-1H-2,9-diazafluorene}

(120) 2-propionyl-{1,1-[3-(dimethylamino-(4-chlorophenyl)methyl)-pentamethylene]-3,4-dihydro-1H-2,9-diazafluorene}

(121) 2-(1-benzothien-3-ylcarbonyl)-{1,1-[3-(dimethylamino-(4-chlorophenyl)methyl)-pentamethylene]-3,4-dihydro-1H-2,9-diazafluorene}

(122) 2-cyclopentylcarbonyl-{1,1-[3-(dimethylamino-(4-chlorophenyl)methyl)-pentamethylene]-3,4-dihydro-1H-2,9-diazafluorene}

(123) 2-[(4-fluorophenyl)acetyl]-{1,1-[3-(dimethylamino-(4-chlorophenyl)methyl)-pentamethylene]-3,4-dihydro-1H-2,9-diazafluorene}

(124) 2-(3-chloro-1-benzothien-2-ylcarbonyl)-{1,1-[3-(dimethylamino-(4-chlorophenyl)methyl)-pentamethylene]-3,4-dihydro-1H-2,9-diazafluorene}

(125) 2-cyclopentylcarbonyl-{1,1-[3-(dimethylamino-phenylmethyl)-pentamethylene]-3,4-dihydro-1H-2,9-diazafluorene}

(126) 2-[(3-methoxyphenyl)acetyl]-{1,1-[3-(dimethylamino-(3-fluorophenyl)methyl)-pentamethylene]-3,4-dihydro-1H-2,9-diazafluorene}

(127) 2-(2-phenoxypropanoyl)-{1,1-[3-(dimethylamino-(3-fluorophenyl)methyl)-pentamethylene]-3,4-dihydro-1H-2,9-diazafluorene}

(128) 2-[5-methylbenzothien-2-ylcarbonyl]-{1,1-[3-(dimethylamino-(3-fluorophenyl)methyl)-pentamethylene]-3,4-dihydro-1H-2,9-diazafluorene}

(129) 1-{1,1-[3-(dimethylamino-(3-fluorophenyl)methyl)-pentamethylene]-3,4-dihydro-1H-2,9-diazafluoren-2-yl}-3-methylbutan-1-one (130) 1-{1,1-[3-(dimethylamino-(3-fluorophenyl)methyl)-pentamethylene]-3,4-dihydro-1H-2,9-diazafluoren-2-yl}-3-phenylbutan-1-one (131) 2-(3-phenylpropanoyl)-{1,1-[3-(dimethylamino-(4-chlorophenyl)methyl)-pentamethylene]-3,4-dihydro-1H-2,9-diazafluorene}

(132) 2-[(3-bromophenyl)acetyl]-{1,1-[3-(dimethylamino-(4-chlorophenyl)-methyl)-pentamethylene]-3,4-dihydro-1H-2,9-diazafluorene};

(133) 2-(2-phenoxypropanoyl)-{1,1-[3-(dimethylamino-(4-chlorophenyl)methyl)-pentamethylene]-3,4-dihydro-1H-2,9-diazafluorene};

(134) 1-{1,1-[3-(dimethylamino-(4-chlorophenyl)methyl)-pentamethylene]-3,4-dihydro-1H-2,9-diazafluoren-2-yl}-3-methylbutan-1-one;

(135) (3-phenylpropanoyl)-1-{1,1-[3-(dimethylamino-(4-chlorophenyl)methyl)-pentamethylene]-3,4-dihydro-1H-2,9-diazafluorene};

(136) 2-[(3-methoxyphenyl)acetyl]-{1,1-[3-(dimethylamino-phenylmethyl)-pentamethylene]-3,4-dihydro-1H-2,9-diazafluorene};

(137) 2-(2-phenoxypropanoyl)-{1,1-[3-(dimethylamino-phenylmethyl)-pentamethylene]-3,4-dihydro-1H-2,9-diazafluorene};

(138) 1-{1,1-[3-(dimethylamino-phenylmethyl)-pentamethylene]-3,4-dihydro-1H-2,9-diazafluoren-2-yl}-3-methylbutan-1-one;

(139) 1-{1,1-[3-(dimethylamino-(4-fluorophenyl)methyl)-pentamethylene]-3,4-dihydro-1H-2,9-diazafluoren-2-yl}-2-ethylbutan-1-one;

(140) 2-[(3-methoxyphenyl)acetyl]-{1,1-[3-(dimethylamino-(4-fluorophenyl)methyl)-pentamethylene]-3,4-dihydro-1H-2,9-diazafluorene};

(141) 2-(2-phenoxypropanoyl)-{1,1-[3-(dimethylamino-(4-fluorophenyl)methyl)-pentamethylene]-3,4-dihydro-1H-2,9-diazafluorene};

(142) 1-{1,1-[3-(dimethylamino-(4-fluorophenyl)methyl)-pentamethylene]-3,4-dihydro-1H-2,9-diazafluoren-2-yl}-3-phenylbutan-1-one;

or a salt thereof with a physiologically acceptable acid.

16. A process for preparing a spirocyclic cyclohexane compound as claimed in claim 1 corresponding to formula I

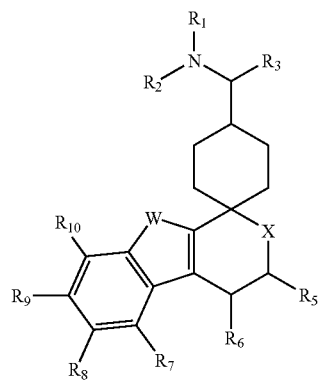

wherein $R^1$ through $R^{10}$, W and X have the respective meanings given in claim 1, said process comprising:

reacting an educt of formula A

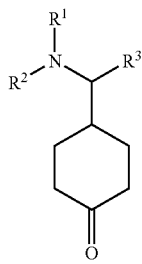

wherein $R^1$ through $R^3$ have the respective meanings given in claim 1, with the addition of an acid or trimethylsilyl ester thereof, in a solvent, with an educt of formula B

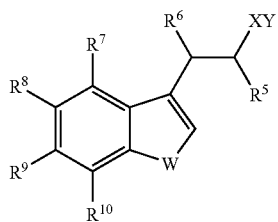

wherein $R^5$ through $R^{10}$, W and X have the respective meanings given in claim 1, and Y denotes H or trimethylsilyl.

17. A process as claimed in claim 16, wherein an educt of formula A is reacted with an educt of formula B with addition of trifluoromethanesulfonic acid trimethylsilyl ester, trifluoromethanesulfonic acid, acetic acid, phosphoric acid, methanesulfonic acid or trifluoroacetic acid, in a solvent selected from the group consisting of dichloroethane, methylene chloride, chloroform, acetonitrile, diethyl ether or nitromethane.

18. A process for preparing a compound as claimed in claim 1, corresponding to formula I

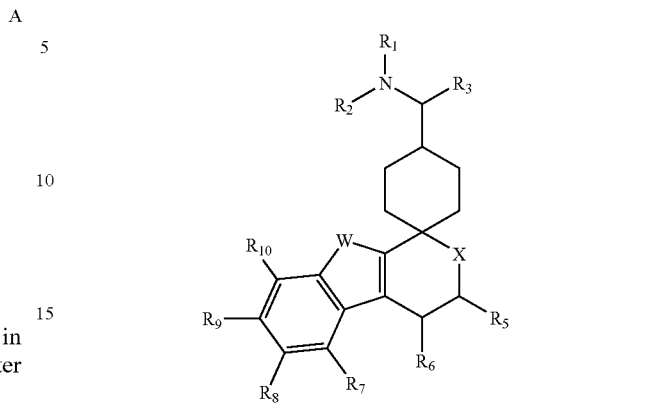

wherein $R^1$ through $R^{10}$ and W have the respective meanings given in claim 1, X denotes $NR^{17}$, $R^{17}$ denotes $COR^{12}$ or $SO_2R^{12}$, and $R^{12}$ has the meaning given in claim 1, said process comprising:
  reacting a compound corresponding to formula I wherein X denotes NH with an anhydride or an acid chloride, and with the addition of a base.

19. A process as claimed in claim 18, wherein said base is triethylamine, and said reaction is carried out under microwave irradiation.

20. A composition comprising a compound as claimed in claim 1, and at least one pharmaceutically acceptable carrier, additive or auxiliary substance.

21. A method of treating a pain in a subject, said method comprising administering to said subject a pharmacologically effective amount of a compound as claimed in claim 1.

22. A method as claimed in claim 21, wherein said pain is acute pain, neuropathic pain or chronic pain.

* * * * *